(12) United States Patent
McClellan

(10) Patent No.: US 9,398,903 B2
(45) Date of Patent: Jul. 26, 2016

(54) KNOTLESS LOCKING TISSUE FASTENING SYSTEM AND METHOD

(76) Inventor: William T. McClellan, Morgantown, WV (US)

( * ) Notice: Subject to any disclaimer, the term of this patent is extended or adjusted under 35 U.S.C. 154(b) by 770 days.

(21) Appl. No.: 13/636,067

(22) PCT Filed: Mar. 21, 2011

(86) PCT No.: PCT/US2011/029204
§ 371 (c)(1),
(2), (4) Date: Sep. 19, 2012

(87) PCT Pub. No.: WO2011/116379
PCT Pub. Date: Sep. 22, 2011

(65) Prior Publication Data
US 2013/0012990 A1    Jan. 10, 2013

Related U.S. Application Data

(60) Provisional application No. 61/315,875, filed on Mar. 19, 2010.

(51) Int. Cl.
*A61B 17/10* (2006.01)
*A61B 17/04* (2006.01)
*A61B 17/064* (2006.01)
(Continued)

(52) U.S. Cl.
CPC ......... *A61B 17/0401* (2013.01); *A61B 17/0469* (2013.01); *A61B 17/0643* (2013.01); *A61B 17/823* (2013.01); *A61B 17/06166* (2013.01); *A61B 2017/0404* (2013.01); *A61B 2017/0414* (2013.01); *A61B 2017/0417* (2013.01); *A61B 2017/0419* (2013.01); *A61B 2017/0464* (2013.01); *A61B 2017/06042* (2013.01); *A61B 2017/06176* (2013.01)

(58) Field of Classification Search
None
See application file for complete search history.

(56) References Cited

U.S. PATENT DOCUMENTS

| 2,746,324 A | 5/1956 | Beardsley |
| 3,129,919 A | 4/1964 | Evans |
| 3,258,040 A | 6/1966 | Evans |

(Continued)

FOREIGN PATENT DOCUMENTS

| WO | WO 96/04871 A1 | 2/1996 |
| WO | WO 96/41581 A1 | 12/1996 |
| WO | WO 2010/108050 | 9/2010 |

OTHER PUBLICATIONS

Written Opinion in PCT/US2011/029204, Nov. 25, 2011, 4 pages.
(Continued)

*Primary Examiner* — Robert Lynch
(74) *Attorney, Agent, or Firm* — Andrew D. Wright; Roberts Mlotkowski Safran & Cole, P.C.

(57) ABSTRACT

Systems and methods for fastening tissue include a tissue fastening device comprising an elongate element and a delivery device including a cone, suture, and needle arranged at a delivery end of the elongate element. At least one of the tissue locking features and a tissue lock device are arranged at an end of the elongate element opposite the delivery end. The system includes a locking feature near the delivery end, and a lock device having a mating feature that corresponds to the locking feature. When the delivery device is passed through the lock device, the mating feature engages the locking feature and locks the lock device in an axial direction along the elongate element.

17 Claims, 19 Drawing Sheets

(51) Int. Cl.
*A61B 17/82* (2006.01)
*A61B 17/06* (2006.01)

(56) References Cited

U.S. PATENT DOCUMENTS

| | | | |
|---|---|---|---|
| 3,462,802 A * | 8/1969 | Merser | B65D 63/1081 |
| | | | 24/16 PB |
| 3,528,142 A | 9/1970 | Valdemar | |
| 3,541,591 A | 11/1970 | Hoegerman | |
| 3,570,497 A | 3/1971 | Lemole | |
| 3,584,525 A | 6/1971 | Caveney et al. | |
| 3,588,963 A * | 6/1971 | Moberg | G09F 3/14 |
| | | | 24/16 PB |
| 3,641,629 A | 2/1972 | Beardsley | |
| 3,661,187 A | 5/1972 | Caveney | |
| 3,664,345 A | 5/1972 | Dabbs et al. | |
| 3,802,438 A * | 4/1974 | Wolvek | 606/232 |
| 3,837,373 A | 9/1974 | Beardsley | |
| 3,865,156 A | 2/1975 | Moody et al. | |
| 3,872,547 A | 3/1975 | Caveney et al. | |
| 3,946,769 A | 3/1976 | Caveney et al. | |
| 3,976,079 A | 8/1976 | Samuels et al. | |
| 3,976,108 A | 8/1976 | Caveney et al. | |
| 4,004,618 A | 1/1977 | Turek | |
| 4,473,925 A | 10/1984 | Jansen | |
| 4,498,506 A | 2/1985 | Moody et al. | |
| 4,510,977 A | 4/1985 | Crowley | |
| 4,535,764 A | 8/1985 | Ebert | |
| 4,570,340 A | 2/1986 | Shaw | |
| 4,607,867 A | 8/1986 | Jansen | |
| 4,646,591 A | 3/1987 | Jansen | |
| 4,688,561 A | 8/1987 | Reese | |
| 4,730,615 A | 3/1988 | Sutherland et al. | |
| 4,741,330 A | 5/1988 | Hayhurst | |
| 4,750,492 A | 6/1988 | Jacobs | |
| 4,813,416 A | 3/1989 | Pollak et al. | |
| 4,862,928 A | 9/1989 | Caveney et al. | |
| 4,887,334 A | 12/1989 | Jansen et al. | |
| 4,896,402 A | 1/1990 | Jansen et al. | |
| 4,930,548 A | 6/1990 | Turek et al. | |
| 4,950,284 A | 8/1990 | Green et al. | |
| 5,053,047 A | 10/1991 | Yoon | |
| 5,065,798 A | 11/1991 | Alletto et al. | |
| 5,123,456 A | 6/1992 | Jansen | |
| 5,127,446 A | 7/1992 | Marelin | |
| 5,129,350 A | 7/1992 | Marelin | |
| 5,144,989 A | 9/1992 | Mika et al. | |
| 5,193,250 A * | 3/1993 | Caveney | B65D 63/1072 |
| | | | 24/16 PB |
| 5,205,328 A | 4/1993 | Johnson et al. | |
| 5,269,783 A | 12/1993 | Sander | |
| 5,303,571 A | 4/1994 | Quinn et al. | |
| 5,318,566 A | 6/1994 | Miller | |
| 5,322,091 A | 6/1994 | Marelin | |
| 5,330,489 A | 7/1994 | Green et al. | |
| 5,356,412 A | 10/1994 | Golds et al. | |
| 5,356,417 A | 10/1994 | Golds | |
| 5,366,461 A | 11/1994 | Blasnik | |
| 5,368,261 A | 11/1994 | Caveney et al. | |
| 5,386,856 A | 2/1995 | Moody et al. | |
| 5,413,585 A | 5/1995 | Pagedas | |
| 5,423,821 A | 6/1995 | Pasque | |
| 5,452,523 A | 9/1995 | Jansen | |
| 5,462,542 A | 10/1995 | Alesi, Jr. | |
| 5,483,998 A | 1/1996 | Marelin et al. | |
| 5,488,760 A | 2/1996 | Jansen | |
| 5,500,000 A | 3/1996 | Feagin et al. | |
| 5,566,726 A | 10/1996 | Marelin | |
| 5,595,220 A | 1/1997 | Leban et al. | |
| 5,643,295 A | 7/1997 | Yoon | |
| 5,665,109 A | 9/1997 | Yoon | |
| 5,735,877 A * | 4/1998 | Pagedas | 606/232 |
| 5,743,310 A | 4/1998 | Moran | |
| 5,755,084 A | 5/1998 | Dekker | |
| 5,766,218 A | 6/1998 | Arnott | |
| 5,832,964 A | 11/1998 | Joshi | |
| 5,850,674 A | 12/1998 | Jansen | |
| 5,972,006 A | 10/1999 | Sciaino, Jr. | |
| 6,014,792 A | 1/2000 | Marelin et al. | |
| 6,015,428 A * | 1/2000 | Pagedas | 606/232 |
| 6,030,410 A | 2/2000 | Zurbrugg | |
| 6,063,106 A | 5/2000 | Gibson | |
| D430,781 S | 9/2000 | Hillegonds | |
| 6,200,318 B1 | 3/2001 | Har-Shai et al. | |
| 6,202,706 B1 | 3/2001 | Leban | |
| 6,206,053 B1 | 3/2001 | Hillegonds | |
| 6,260,704 B1 | 7/2001 | Jansen et al. | |
| 6,270,517 B1 * | 8/2001 | Brotz | A61B 17/064 |
| | | | 606/215 |
| 6,287,307 B1 | 9/2001 | Abboudi | |
| 6,354,336 B1 | 3/2002 | Leban | |
| 6,481,467 B2 | 11/2002 | Czebatul et al. | |
| 6,516,804 B1 | 2/2003 | Hoffman | |
| D473,773 S | 4/2003 | Hillegonds et al. | |
| 6,705,002 B1 | 3/2004 | Dukes et al. | |
| 6,840,289 B2 | 1/2005 | Hillegonds | |
| 7,043,315 B2 | 5/2006 | Litao | |
| 7,089,970 B2 | 8/2006 | Bernard | |
| 7,168,331 B1 | 1/2007 | Bernard et al. | |
| 7,255,700 B2 | 8/2007 | Kaiser et al. | |
| 7,299,830 B2 | 11/2007 | Levin et al. | |
| 7,334,610 B2 | 2/2008 | Levin et al. | |
| 7,361,179 B2 | 4/2008 | Rousseau et al. | |
| 7,373,695 B2 | 5/2008 | Caveney et al. | |
| 7,438,094 B2 | 10/2008 | Hillegonds et al. | |
| 7,455,683 B2 | 11/2008 | Geissler et al. | |
| 7,458,398 B2 | 12/2008 | Hillegonds et al. | |
| 7,484,274 B2 | 2/2009 | Nelson et al. | |
| 7,600,721 B2 | 10/2009 | Vermeer et al. | |
| 7,650,680 B2 | 1/2010 | Stillings et al. | |
| 7,651,509 B2 | 1/2010 | Bojarski et al. | |
| 7,708,759 B2 | 5/2010 | Lubbers et al. | |
| 2003/0195531 A1 | 10/2003 | Gardiner et al. | |
| 2004/0059357 A1 | 3/2004 | Koseki | |
| 2005/0131430 A1 | 6/2005 | Ravikumar | |
| 2005/0166990 A1 | 8/2005 | Stillings et al. | |
| 2006/0116719 A1 | 6/2006 | Martinek | |
| 2006/0254031 A1 | 11/2006 | DeMik et al. | |
| 2006/0276809 A1 | 12/2006 | Oliveira | |
| 2007/0055258 A1 | 3/2007 | Hansen | |
| 2007/0056145 A1 | 3/2007 | Stillings et al. | |
| 2007/0290100 A1 | 12/2007 | Caveney | |
| 2008/0071279 A1 | 3/2008 | Allinniemi et al. | |
| 2009/0078331 A1 | 3/2009 | DeMik | |
| 2009/0078597 A1 | 3/2009 | Abbott et al. | |
| 2009/0114308 A1 | 5/2009 | Marelin et al. | |
| 2009/0228022 A1 | 9/2009 | McClellan | |
| 2009/0242069 A1 | 10/2009 | Segroves | |
| 2009/0271956 A1 | 11/2009 | Nelson et al. | |
| 2010/0139805 A1 | 6/2010 | Sledzinski | |
| 2010/0268273 A1 | 10/2010 | Albertorio et al. | |
| 2011/0022050 A1 | 1/2011 | McClellan | |
| 2011/0029001 A1 | 2/2011 | Trieu et al. | |
| 2011/0295257 A1 | 12/2011 | McClellan et al. | |

OTHER PUBLICATIONS

International Search Report in PCT/US2011/029204, Nov. 25, 2011, 5 pages.
International Preliminary Report on Patentability in PCT/US2011/029204, Sep. 21, 2012, 16 pages.

* cited by examiner

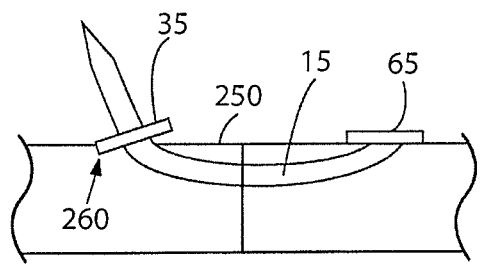
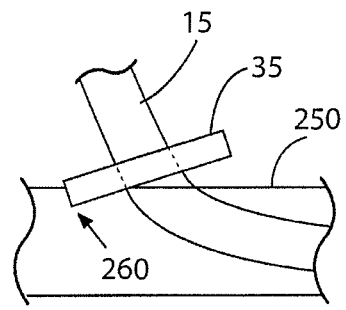
FIG. 26A                FIG. 26B
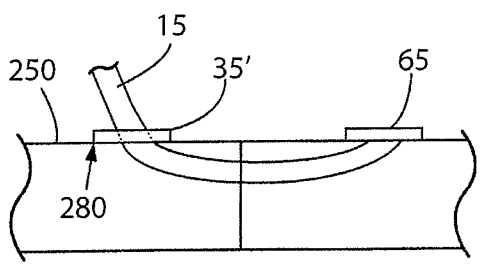
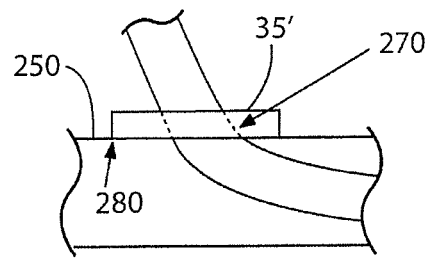
FIG. 28A                FIG. 28B

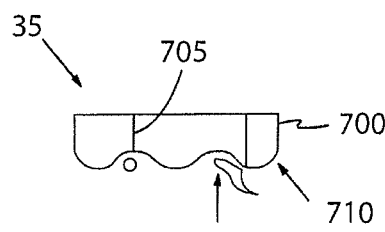
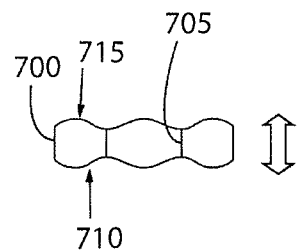
FIG. 34A             FIG. 34B
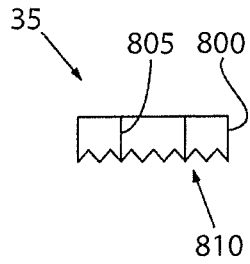
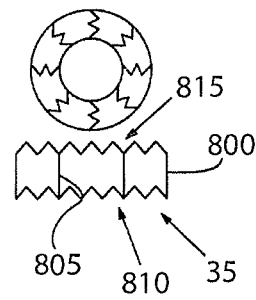
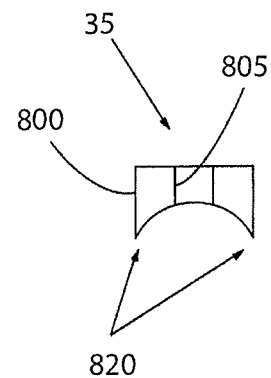
FIG. 35A       FIG. 35B       FIG. 35C
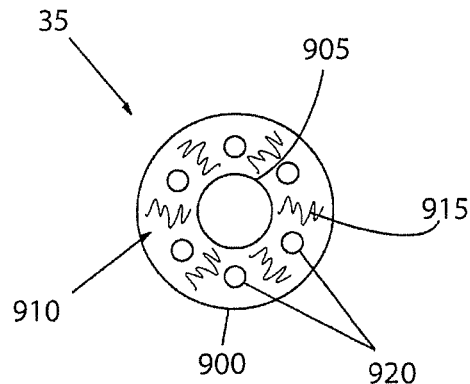
FIG. 36

KNOTLESS LOCKING TISSUE FASTENING SYSTEM AND METHOD

CROSS REFERENCE TO RELATED APPLICATIONS

This application claims priority to U.S. Provisional Application No. 61/315,875, filed Mar. 19, 2010, the contents of which are incorporated by reference herein in their entirety.

BACKGROUND OF THE INVENTION

1. Field of the Invention

The invention generally relates to medical devices and procedures, and more particularly to devices and methods for tendon, ligament, and soft tissue repair, bone, sternum, fascia, closure and/or reinsertion.

2. Discussion of Background Information

Conventional methods for tendon, ligament, soft tissue repair, sternum, fascia or bone (now after called "tissue") often involve extensive suturing of the tissue being repaired. For example, in the case of tendon repair, one known method involves passing a first suture into and out of a first portion of the tendon numerous times, resulting in two free ends of the suture extending from the cut end of the first tendon portion. A second suture is similarly arranged in a second tendon portion. The free ends of the first and second sutures are tied (e.g., knotted) together to affix the cut ends of the tendon portions together. Another example involved sternal repair following heart surgery in which steel wire is passed between the ribs and twisted/crimped together to achieve stability between tohe bone edges.

However, such methods have numerous drawbacks. The act of passing the suture into and out of the tendon (e.g., typically at least six times per tendon portion) causes trauma to the tendon, thereby increasing the chance for infection. Furthermore repeated trauma to the tendon by excessive handling may create excessive damage to tendon/ligament/tissue vasculature which may compromise repair. Also, the knots of the sutures artificially increase the dimension of the tendon at the repair site, which creates increased friction at the repair site and/or tendon pulley interface. Increased friction at this interface increases the opportunity for tendon failure during loading. Even further, the strength of the repair is dependent upon the knots, which may slip over time (e.g., due to surgical error). Conventional suture-based repair methods may disadvantageously impair the vascularity of the tendon and have increased tendon diameter at the repair site. Traditional suture repair requires extensive exposure, manipulation, handling, and needle penetration of the tendon.

For sternal reconstruction the wires are subject to stress forces caused by sterna movement from breathing. This leads to metal fatigue and fracturing. Wire integrity loss can cause sternal infection and non-union. This occurs in 5% of all open heart surgeries. Furthermore there have been reports of allergy to metals which often prompts the removal of wires and risk exposure by the patient. The wires are also dependent upon the skill of the surgeons as they tighten the wires. Too many turns in the wire may unnecessarily weaken the wire and subject it to future failure. Sternal plating system have been developed, much like plates for fractured bones, however there are many hurdles in the success of the plates. They are cumbersome and difficult to apply, the cardiothoracic surgeons are usually not trained or comfortable with the application, typically they are reserved for sternal dehiscence cases, and they are expensive.

A variety of techniques have been proposed to close tissue. Most of which involve suture in one fashion or another. Steel wire, barbed suture, and sternal plating systems are alternative to traditional methods. These alternatives have to capacity to be stronger, eliminate knots, and diminish cross sectional area. However they bear the burden of being technically difficult, expensive, and have not provided improved outcome. Barbed filaments provide an alternative to knot-based repair techniques. According to known methods, a single barbed filament is passed into and out of the portions of the tendon, thereby drawings the tendon portions together. Barbs on the exterior of the barbed filament engage the tendon portions internally, thereby resisting separation of the drawn-together tendon portions. Repairs using barbed filaments can be knotless, have the potential for a lower tendon profile at the site of the repair, and have the potential for equivalent strength when compared to knot-based repairs. However, techniques using barbed filaments can be more traumatic to the tendon than traditional repairs, may increase the risk of infection and/or impair the vascularity of the tendon, and are technically demanding.

Accordingly, there exists a need in the art to overcome the deficiencies and limitations described hereinabove.

SUMMARY OF THE INVENTION

In accordance with a first aspect of the invention, there is a system for fastening tissue include a tissue fastening device comprising an elongate element and a delivery device including a cone, suture, and needle arranged at a delivery end of the elongate element. At least one of tissue locking features and a tissue lock device are arranged at an end of the elongate element opposite the delivery end. The system includes a locking feature near the delivery end, and a lock device having a mating feature that corresponds to the locking feature. When the delivery device is passed through the lock device, the mating feature engages the locking feature and locks the lock device in an axial direction along the elongate element.

The lock device may be integral with the at least one of tissue locking features and the tissue lock device. The tissue lock device may comprise a groove, and the elongate element may comprise a head element that fits within the groove such that a top surface of the head element is substantially flush with a top surface of the tissue lock device. The tissue lock device may comprise a protrusion in the groove, the head element may comprise an indentation that corresponds to the protrusion, and the protrusion may engage the groove to prohibit axial movement of the head element out of the groove when the head element is arranged in the groove. The head element may spin within the groove when the protrusion engages the groove.

In embodiments, the delivery device is passed through the lock device by one of: threading the needle through a hole in the lock device; and passing the suture through a radial slit and into a though-hole in the lock device.

According to aspects of the invention, the tissue lock device is connected to the lock device by a swivel mechanism that permits relative rotational movement between the lock device and the tissue lock device.

In accordance with further aspects of the invention, the elongate element is structured and arranged as a running suture, a tissue lock device is arranged at a beginning of the running suture, and a plurality of lock devices are arranged on an engage the elongate element at a plurality of locations along the running suture.

In embodiments, the lock device comprises an angled hole that is structured and arranged to receive and engage the elongate element at an acute angle relative to a central axis of the lock device. The lock device may comprise an annular body comprising tapered sidewalls and rounded corners.

According to aspects of the invention the lock device comprises an annular body and a swivel head rotatably attached within the annular body, wherein the swivel head is structured and arranged to receive and engage the elongate element at an acute angle relative to a central axis of the annular body.

In accordance with additional aspects of the invention, the locking feature comprises at least one tapered element having a narrow end and wide end on the elongate element, the lock device comprises a cone comprising a rim structured and arranged to sit against tissue, angled sidewalls, and a hole, and the hole is larger than the narrow end of the tapered element and smaller than the wide end of the tapered element.

In embodiments, the elongate element comprises a groove and the locking features are arranged within the groove such that the locking features are not on an outermost surface of the elongate element. The elongate element may have an oval or round cross sectional profile including the groove; and the lock device may comprise a member having an annulus comprising the mating feature, the annulus and mating feature corresponding in shape to oval or round cross sectional profile including the groove.

According to aspects of the invention, lock device comprises a plunger that is structured to engage the elongate element when depressed inward or pulled outward, the plunger preventing the lock device from moving along the elongate element when engaged.

In accordance with even further aspects of the invention the lock device comprises one of: an undulating bottom surface having rounded concave and convex portions that are structure and arranged to lie against the tissue to reduce pressure on portions of the tissue within the concave portions; a sawtooth profile bottom surface that is structured and arranged to lie against and dig into the tissue to secure the lock device to the tissue; and surface roughening and/or small holes that promote the in-growth of tissue into the lock device.

In embodiments, the lock device comprises an annular member having a through hole and a radial slit, the radial slit being larger than the suture and smaller than the elongate member, such that the suture may be passed through the slit and into the hole. The system may further comprise a gun comprising a magazine for holding a plurality of the lock devices each having the axial slit, and an actuator for pushing one of the lock device outward from the gun with the axial slit facing outward.

In accordance with a another aspect of the invention, there is a method of tissue repair comprising: inserting a delivery end of a tissue fastening device through a first tissue until at least one of tissue locking features and a tissue lock device engages the first tissue; inserting the delivery end of the tissue fastening device through a second tissue; inserting the delivery end of the tissue fastening device through a lock device; and locking the lock device on an elongate element of the tissue fastening device, such that the first tissue is fastened to the second tissue via the tissue fastening device and the lock device.

In the method, the tissue fastening device comprises a cone, suture, and needle at the delivery end. The method may further include: inserting the delivery end through the first tissue again; inserting the delivery end through the second tissue again; inserting the delivery end of the tissue fastening device through a second lock device; locking the second lock device on the elongate element of the tissue fastening device; and cutting the elongate element substantially flush with the lock device, such that the delivery end is detached.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIGS. 1-38 show elements of systems and methods according to aspects of the invention.

DETAILED DESCRIPTION OF EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The invention generally relates to medical devices and procedures, and more particularly to devices and methods for tissue repair. In embodiments, there is a Knotless Locking Tissue Fastening System comprising the tissue fastening device and its delivery device, the lock device, the tissue lock device, and applications. The Knotless Locking Tissue Fastening System may be comprised of the tissue fastening device with or without a delivery device, and the lock device. The system may also include a tissue lock device, an assembly device, a separate dilator device, or an alignment device. Implementations of the invention may be used for, but are not limited to: closure of the sternum following cardiac surgery; closure of thoracic incisions following thoracic surgery; tendon repair; ligament repair; closure of abdominal fascia; intradermal closure of skin or subcutaneous tissue and fascia; facial rejuvenation; eyelid suspension; and, repair of bone fractures. In this manner, implementations of the invention provide an effective system and method for tissue repair that overcome the above-described deficiencies and limitations of the prior art.

Exemplary Systems

Figure 1:
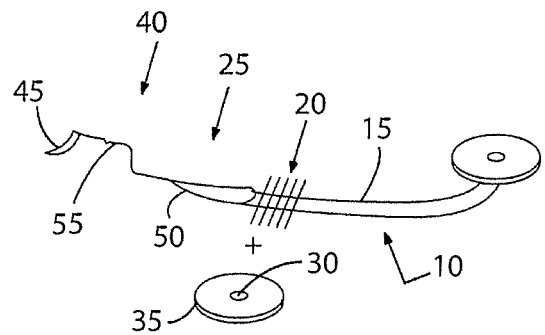
Figure 2A:
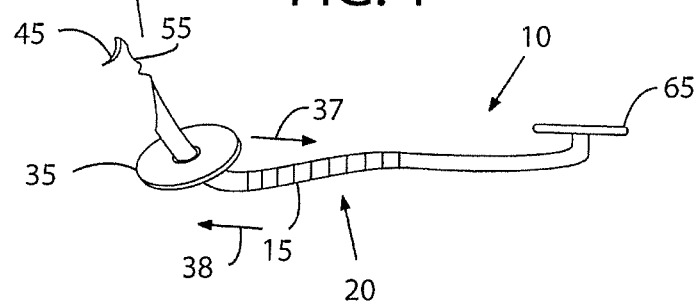
Figure 2B:
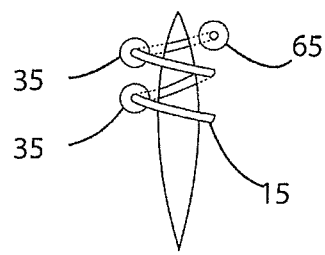
Figure 3:
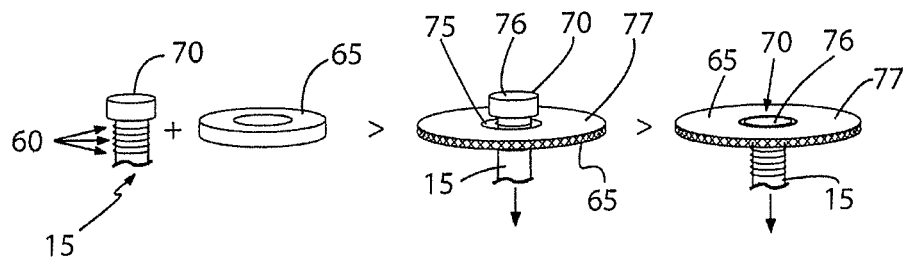

Referring to FIGS. 1-3, the tissue fastening device 10 may be comprised of a solid or hollow length of material (e.g., elongate element) 15 that can be bioabsorbable or permanent in its material composition. The device can have any cross-sectional shape necessary to optimize the application, including, but not limited to, circular, oval, flat, etc. The tissue fastening device 10 may be defined by the presence of locking features 20 near the delivery end 25 that can engage mating features 30 on a lock device 35 to prevent movement of the tissue fastening device 10 relative to the lock device 35. These features 20, 30 may include but are not limited to the following: raised ridges for a one-way ratcheting lock, screw threads for a screw lock, holes for a pin or peg lock, nano-particles (e.g., substantially oppositely aligned nano-sized filaments, scales, etc.), or no features for locking by compression, crimping, adhesives, or soldering. These locking features 20, 30 on the dilator end 25 of the tissue fastening device 10 and on the lock device 35 may be male or female in nature, e.g., may be structured and arranged to engage each other in a complimentary locking nature. For example, the locking features 20 may be a male portion of a one-way ratchet system, and the features 30 may be a female portion of the one-way ratchet system that corresponds to the male portion such that the lock device 35 may be moved in a first axial direction 37 along the elongate element 15 while being inhibited or prevented from traveling in a second axial direction 38, opposite the first axial direction 37, along the elongate element 15, as shown in FIG. 2A. In this manner, the tissue fastening device 10 may be used as a zip-suture in which the elongate element 15 is passed through tissue and the locking device 35 is slid down the elongate element until the lock device 35 is secure against the tissue.

As depicted in FIG. 2B, the elongate element 15 may be repeatedly passed through tissue with plural lock devices 35 arranged on the elongate member at plural different locations to create a running and uninterrupted closure. In this manner, the tissue fastening device 10 provides a fast and secure suture that avoids the problems of knot failure associated with conventional suturing. In further embodiments, the diameter of the elongate element 15 may be larger than that of a traditional suture to prevent pull through. For example, the elongate member 15 may have a diameter of about 1 mm to 1 cm, although the invention is not limited to this size and any suitable size(s) may be employed within the scope of the invention.

The tissue fastening device 10 may be attached to a delivery device 40 comprising a curved or straight needle 45 either directly connected to a cone dilator 50 or connected to a braided or monofilament suture 55 that is connected to a cone dilator 50, which in turn is connected to the newly described tissue fastening device 10. The connections may be formed by swaging or any other suitable technique. The delivery device may also include an automated or semi-automated mechanism separate from the components of the delivery device 40 described above, for placing the tissue fastening device 10 in its appropriate position within tissue. The tissue fastening device 10 and lock device 35 will each incorporate tissue locking features or an integrated or separate tissue lock device 65 that will engage with tissue in order to prevent movement of either relative to the tissue, and therefore securely hold tissue in position. These tissue locking features or the tissue lock device 65 may include but are not limited to the following: a crossbar or pledget, one or more barbs, or one or more hooks.

Figure 4A:
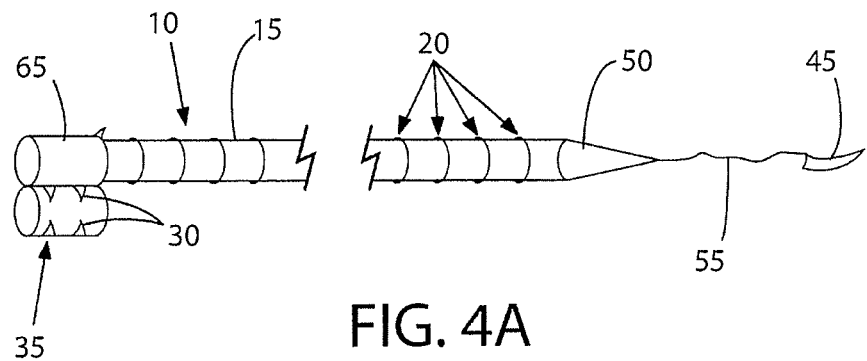
Figure 5:
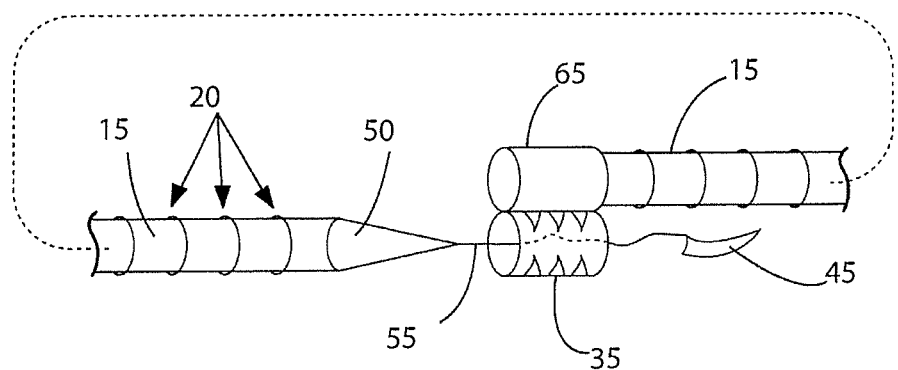
Figure 6:
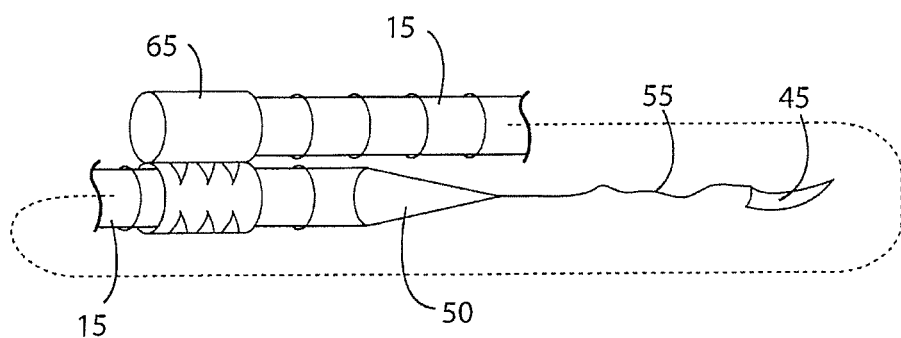
Figures 4B, 4C:
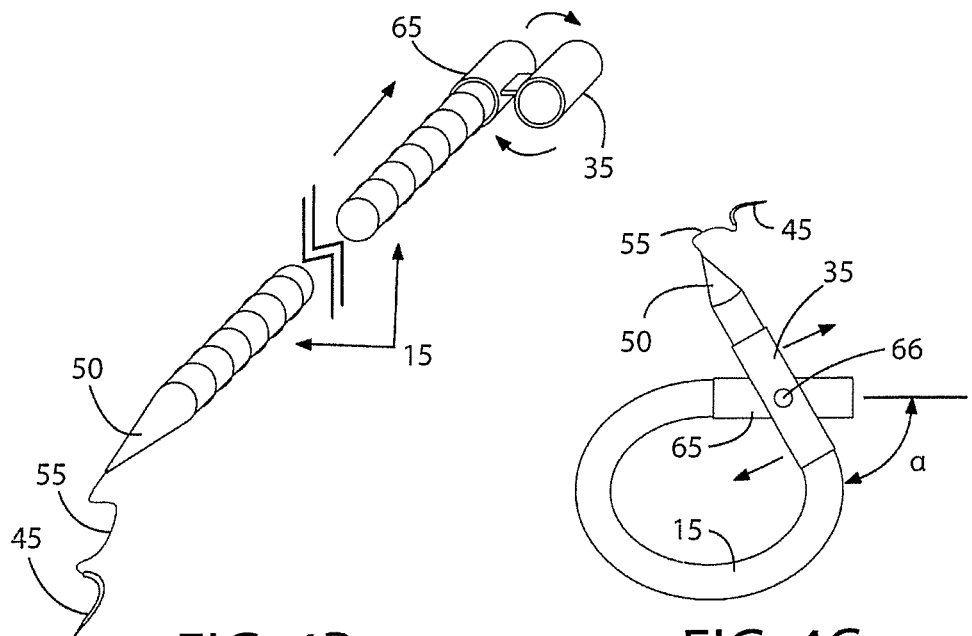
Figure 4D:
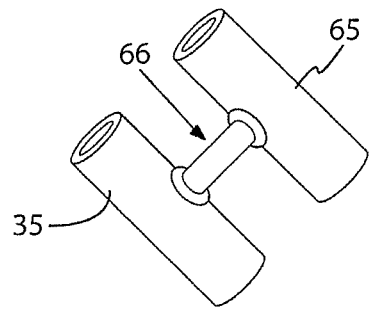
Figures 4E, 4F:
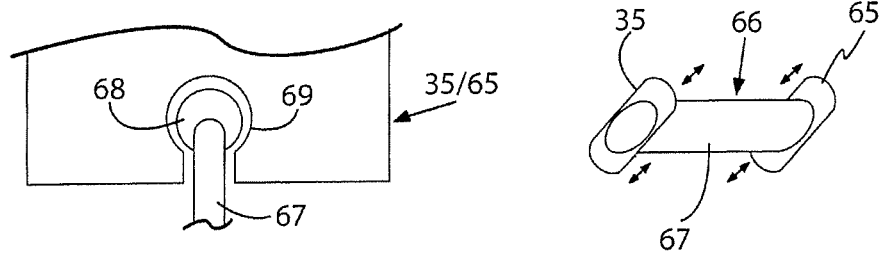

The tissue fastening device 10, lock device 35, and potentially tissue lock device 65 may be separate devices, or may be integrated as a single Integrated tissue fastening device that is locked by assembling the tissue fastening device portion of the Integrated tissue fastening device and the lock device portion, as a loop (see, e.g., FIGS. 4A-4F, 5, 6). In embodiments, the lock device 35 and tissue lock device 65 may be integrally formed such that there is little or no relative movement between these elements, as depicted in FIGS. 4A, 5, and 6.

In other embodiments, the lock device 35 and tissue lock device 65 are separately formed and connected in a manner that permits relative movement between the lock device 35 and tissue lock device 65. For example, as shown in FIGS. 4B-4F, a swivel mechanism 66 may connect the lock device 35 and tissue lock device 65 while permitting a swivel action between the lock device 35 and tissue lock device 65. The swivel action permits a through bore of the lock device 35 to rotate an angle α relative to a through bore of the tissue lock device 65, which permits the lock device 35 to line up at an optimal angle at the end of the elongate element 15, which provides a loop in the elongate element 15 while avoiding placing undue tension on the system.

In embodiments, the swivel mechanism 66 comprises a rod 67 having opposite ends 68 that are engaged in respective cavities 69 of the lock device 35 and tissue lock device 65. The ends 68 and cavities 69 may be sized such that an end 68 cannot pull out of a cavity 69, but with sufficient play such that the end 68 can rotate within the cavity 69. In further embodiments, the end 68 and cavity 69 may be structured and arranged to provide an amount of wiggle room such that in addition to rotation with the cavity 69, the rod may also undergo a limited amount of angular displacement relative to the cavity 69. In this manner, a loose joint may be provided between the rod 67 and each of the lock device 35 and tissue lock device 65 to avoid any binding between the lock device 35 and tissue lock device 65, which binding may otherwise cause undesired pressure on adjacent tissue. Accordingly, in implementations, the swivel mechanism 66 permits the tissue fastening device to conform to the adjacent tissue, rather than causing the tissue to conform to the device.

In embodiments, the swivel mechanism 66 may permit 360° rotation between the lock device 35 and tissue lock device 65. In other embodiments, the swivel mechanism 66 may be provided with limit stops or other structure(s) for limiting the rotational movement of the lock device 35 relative to the tissue lock device 65 to a predefined amount.

Multiple tissue fastening devices 10 may also be connected in series as a Linked tissue fastening device, where each connected tissue fastening device can accommodate its own lock device, as well as its own tissue locking features or tissue fastening device. Each Device within the Linked tissue fastening device can be disconnected from the others by some method including but not limited to cutting. Ultimately, by joining the lock device to the tissue fastening device, with its tissue locking features or tissue lock device, a secure joining of any tissues can be performed.

The Knotless Locking Tissue Fastening System may comprise the following parts: a tissue fastening device 10 with tissue locking features 60 and/or a separate or integrated tissue lock device 65, and a lock device 35. The elongate body of the tissue fastening device 10 can have a circular, oval, flat, or other cross-sectional shape depending on the needs of the specific tissue application, and may or may not be connected to a delivery device 40. All of these parts may be integrated in any combination into one or more parts that are mutually dependent on one another for proper delivery into tissue, as well as secure attachment to one another and to tissue.

Figure 7:
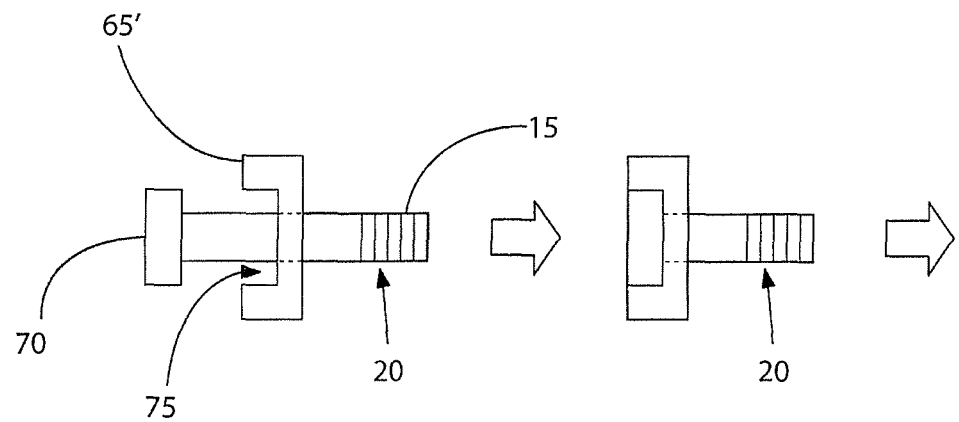

The end of the tissue fastening device can be fitted with integrated tissue locking features 60 and/or a separate tissue lock device 65 as described in the drawings that serve to modify the pressure footprint of the device on tissue. In embodiments, the integrated tissue locking features 60 and/or tissue lock device 65 may serve any number of purposes including but not limited to: preventing pull-through of the tissue fastening device 10, matching the anatomic topography and morphology of the tissue, presenting a lower profile relative to the tissue surface, or redistributing the pressure placed on tissue by the device. As depicted in FIGS. 3 and 7, the tissue fastening device 10 may comprise a head element 70 at one end of the elongate element 15, which head element 70 corresponds in size and shape to a groove 75 of the tissue lock device 65. In this manner, the head element 70 fits flush or countersunk within the tissue fastening device 10, e.g., such that a top surface 76 of the head element 70 is at a same level or lower than a top surface 77 of the tissue lock device 65.

Figure 8:
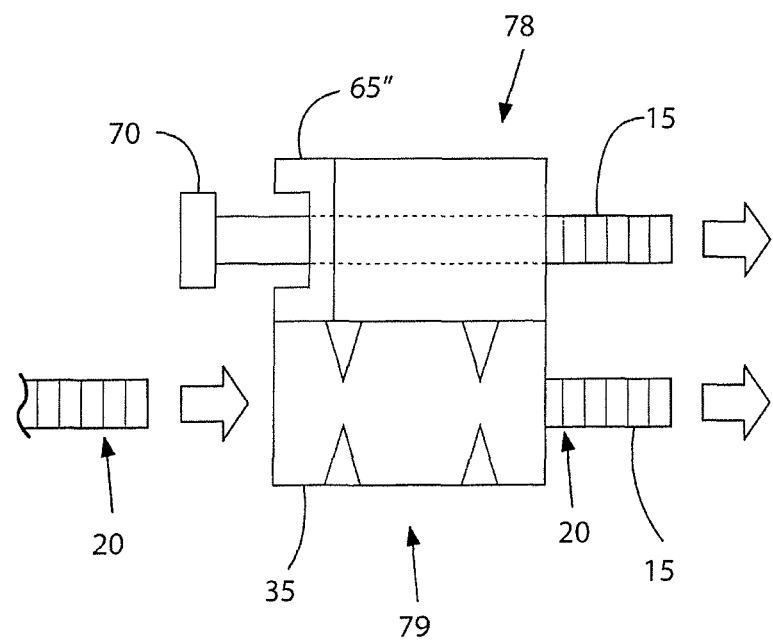

In embodiments of the invention, the head element 70 and elongate body 10 are sized and shaped to correspond to plural different types of tissue lock devices 65. For example, FIG. 7 shows a tissue fastening device 10 engaging a first type of tissue lock device 65' that may be used, for example, for fascial closures. In embodiments, the fascia tissue lock device 65' has a wider base that allows force to be displaced over a greater area. Alternatively, FIG. 8 shows the same tissue fastening device 10 engaging a second type of tissue lock devices 65" that is different from the first type and may be used, for example, as a cardiac zip base. In embodiments, the cardiac zip tissue lock device 65" comprises a first portion 78 for engaging the head element 70 and a second portion 79 comprising a lock device 35. The first portion 78 and second portion 79 may be integrally formed, or may be separately formed and connected to one another. In this way, the tissue fastening device 10 may be used interchangeably with plural different types of tissue lock devices 65 that are structured and arranged for different applications, e.g., tendon attachment, fascial attachment, cardiac attachment, ligament reattachment, etc. For example, an embodiment of the invention may comprise a kit including at least one tissue fastening device 10 and a plurality of different types of tissue lock devices 65, such that a surgeon (or other user) may select the appropriate tissue lock devices 65 to use with the procedure at hand. As an even further example, the kit may come as a pre-packaged kit of ready-to-use parts, which kit is opened during surgery and from which the surgeon (or other personnel) select and use the appropriate parts.

Any of the elements (e.g., parts) described herein (e.g., the tissue fastening device 10, the lock device 35, the tissue lock devices 65, etc.) can be made of any suitable material, such as, for example, permanent material, bioabsorbable material, etc.

These parts may have small pores or holes or other features intended to allow in-growth of blood vessels and/or connective tissue. For example, any of the elements described herein may be provided with pores (e.g., holes) and/or indentations having dimensions suitable to allow for in-growth of blood vessels or other connective tissue into the system to improve anchoring of the parts within the tissue. The pores and/or indentations may be created by laser or other suitable device or manufacturing method.

These parts may be immunologically and/or chemically enhanced to regulate, modify, or supplement tissue healing. For example, any of the elements described herein may be coated or impregnated with growth hormone, antibiotic, etc. Alternatively, any of the elements described herein may be devoid of immunological and/or chemical enhancements (e.g., additives) for applications where such enhancements/additives are undesirable.

These parts may be stiff or flexible to the appropriate degree for the given application.

These parts may have reinforcing features or materials added in the form of cross-sectional changes, fibers, wires, or other composites or integrated components to assist in preventing device failure. For example, reinforcing fibers can be added to, or included in, any of the elements described herein. Such fibers may be incorporated into the elements of the system to provide structural reinforcement.

These parts can be joined together in multiple ways not limited to raised ridges for a one-way ratcheting lock, screw threads for a screw lock, holes for a pin or peg lock, nanoparticles (e.g., substantially oppositely aligned nano-sized filaments, scales, etc.), or no features for locking by compression, crimping, adhesives, or soldering. Any of these techniques may be used to fix (e.g., lock) the tissue fastening device to the locking device, such that axial movement of the locking device 35 along the elongate element 15 of the tissue fastening device is substantially limited to a single axial direction such that removal of an installed locking device 35 is substantially prevented. In further embodiments, the tissue fastening device 10 may be axially fixed relative to the locking device 35 using heat (e.g., to deform or melt at least one of the tissue fastening device 10 and the locking device 35), adhesive (e.g., to adhere the tissue fastening device 10 to the locking device 35), or by inserting a shim or wedge between the elongate element 15 and the locking device 35. For example, the shim or wedge may comprise an annular cap that slides over the elongate element 15, and fits between the outer surface of the elongate element 15 and the inner surface of the locking device 35. The friction created between the tight fit of the shim/wedge/cap between the elongate element 15 and the locking device 35 fixes the locking device 35 so that the locking device cannot move axially along the elongate element. The friction fit created by the shim/wedge/cap can be supplemented by heat deformation, adhesive, crimping etc.

Figure 9:
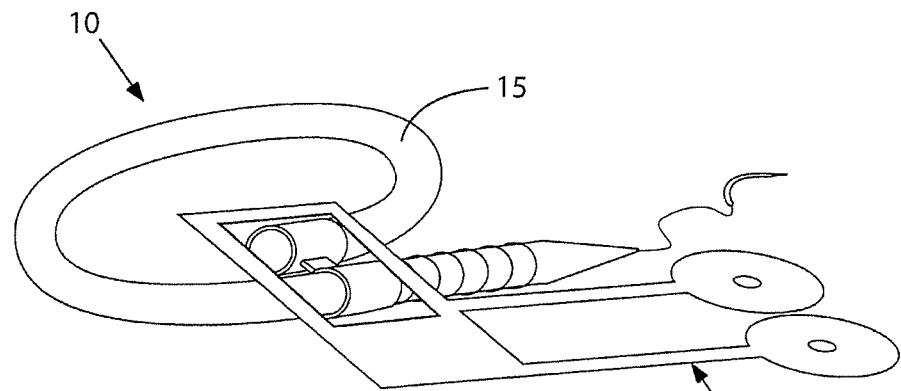
Figure 9:
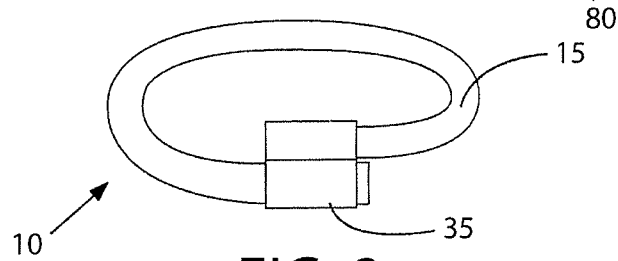

As shown in FIG. 9, assembly of parts to one another may be automated with a separate assembly device 80 that may perform any of but not be limited to the following functions: securely hold the parts, align the parts to one another, coapt the parts to one another, assemble and lock the parts relative to one another, separate the tissue fastening device 10 from its delivery end which consists of the segment from the needle to and including the dilator, monitor and/or control locking conditions such as tension and pressure, or align the tissue portions to be approximated and joined.

For example, the assembly device 80 may be structured and arranged to be used with a tissue fastening device 10 similar to that shown in FIGS. 4-6 and 8, in which the tissue fastening device 10 forms an adjustable-size locking loop in a zip-type arrangement. After the delivery end of the tissue fastening device 10 is passed through and engaged with the lock device 35 (e.g., FIGS. 6 and 9), the assembly device 80 engages the tissue fastening device 10 and lock device 35, pulls the elongate element 15 of the tissue fastening device 10 through the lock device 35 to a predetermined force, and then cuts the elongate element 15 of the tissue fastening device 10 to be flush with the lock device 35. In embodiments, the assembly device 80 comprises a dial (or other selection arrangement) for selectively setting the assembly device 80 to one of a plurality of predetermined forces, e.g., tensioning forces of the elongate element 15. In this manner, the user (e.g., surgeon, etc.) may select the force with which to close the tissue fastening device 10 by manipulating the dial or other selection arrangement. Alternatively, there may be a plurality of assembly devices 80, each configured to operate at a different predetermined force. In this manner, the user (e.g., surgeon, etc.) may select the force with which to close the tissue fastening device 10 by selecting and using the appropriate one of a plurality of assembly devices 80.

In embodiments, the assembly device 80 may comprise a tensioning gun, such as that described in U.S. Patent Application Publication 2011/0022050 the contents of which are incorporated by reference herein in their entirety, and/or International Patent Application Publication No. WO 2010/108050 the contents of which are incorporated by reference herein in their entirety. For example, the assembly device 80 may comprise a tensioning gun used to tighten a suture (i.e., tissue fastening device 10) and/or cut it. In one implementation, the tensioning gun may include handles and jaws. The tensioning gun may be used to tighten a tissue fastening device 10, and may include jaws that are configured to close on the elongate element 15 beside the lock device 35. The user may then squeeze the handles of the tensioning gun. As the handles are squeezed together, the jaws may close on the elongate element 15 beside the lock device 35 (e.g., the male suture next to the female lock), pull it through a few more millimeters and then cut it. The handles may be squeezed to advance the elongate element 15 (e.g., zip suture) in a ratchet-like fashion through the lock device 35 (e.g., female lock). In some embodiments, the tensioning gun may automatically cut the elongate element 15 (e.g., zip suture) after the handles are squeezed. In other embodiments, other controls may be provided to cause the actual cutting step A separate dilator device may be used prior to male device delivery, e.g., prior to passing the elongate element 15 through the tissue, to create a precise pathway for delivery if the constitution of the tissue is of such high density that excessive deformation of the device is possible on delivery. This Dilator will be of similar size and shape to the tissue fastening device. It can be removable so that it creates a tunnel through the intended tissue to be fastened so that the device can be delivered more easily and decrease deformation of the device. This dilator device may perform its function by sharp penetration, drilling, or other methods.

A separate alignment device may be used in order to properly position the various parts and/or the tissue relative to one another in order to achieve optimal tissue approximation.

Figure 10:
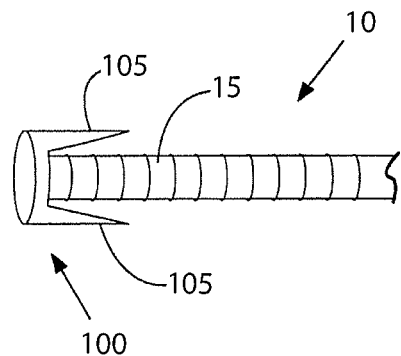
Figure 11:
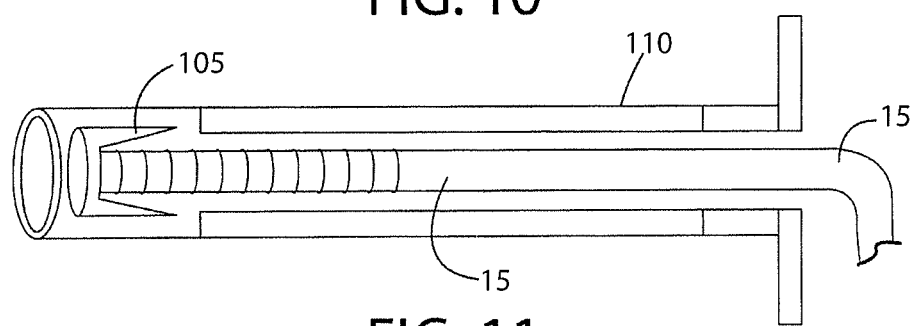
Figure 12:
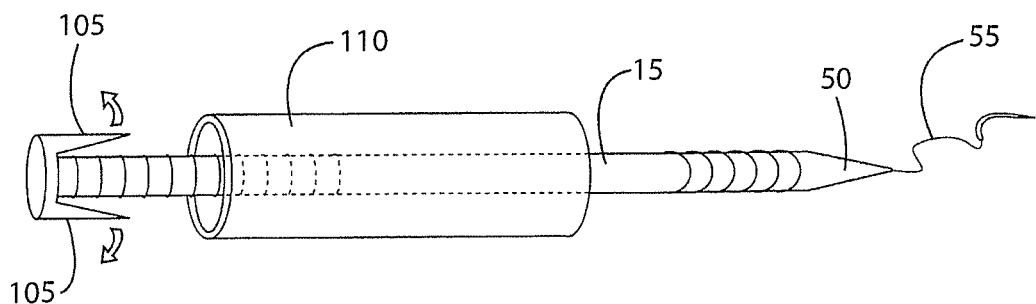

FIGS. 10-12 depict an example of a tissue fastening device 10 that is useable for facial rejuvenation, and other related procedures. As depicted in FIG. 10, a head 100 having barbs 105 is arranged at the end of the elongate body 15 of the tissue fastening device 10. As shown in FIG. 11, a delivery tube 110 is arranged around the tissue fastening device 10, covering the barbs 105. The delivery tube 110 allows the tissue fastening device 10 to be inserted into the tissue while preventing the barbs 105 from engaging the tissue during insertion. When the tissue fastening device 10 is properly located in the tissue, the delivery tube 110 is removed, and the barbs 105 are exposed (e.g., FIG. 12), thereby allowing the barbs 105 to engage the tissue and fix the tissue fastening device 10 to the tissue. The delivery tube 110 may be removed and discarded, or may subsequently be used with another tissue fastening device 10.

In embodiments, the barbs 105 may be formed by cutting (e.g., slicing) the material of the elongate element 15. The elongate element 15 may be composed of a material that causes the barbs 105 to spring outward when cut. The delivery tube 110 may be sized to compress the barbs 105 inward toward the axial center of the elongate element 15 when the delivery tube is positioned around the elongate element 15 and over the barbs 105. In this manner, when the delivery tube 110 is moved to uncover the barbs 105, the barbs 105 spring outward to engage the surrounding tissue.

Figure 13:
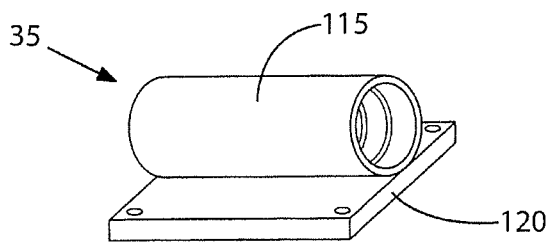

FIG. 13 shows a Locking Device 35 that is configured for use with the tissue fastening device 10 shown in FIGS. 10-12. The locking device 35 comprises a female member 115 connected to a platform 120. The female member 115 has internal locking structures that correspond to external locking structures on the elongate body 15 of the tissue fastening device 10, such that a zip-type locking engagement may be created by inserting the delivery end 25 of the tissue fastening device 10 into the female member of the locking device 35. The platform 120 is arranged to be fastened (e.g., by suturing) to another tissue, such as, for example, a fascia of the skull, or to bone. In this manner, the first tissue that is engaged by the barbs 105 and the second tissue that is attached to the platform 120 may be drawn together by pulling the elongate body 15 of the tissue fastening device 10 through the female member 115 of the locking device 35. Alternatively, the female member 115 may be secured directly to the second tissue (e.g., by suturing) without using a platform 120.

Figure 14:
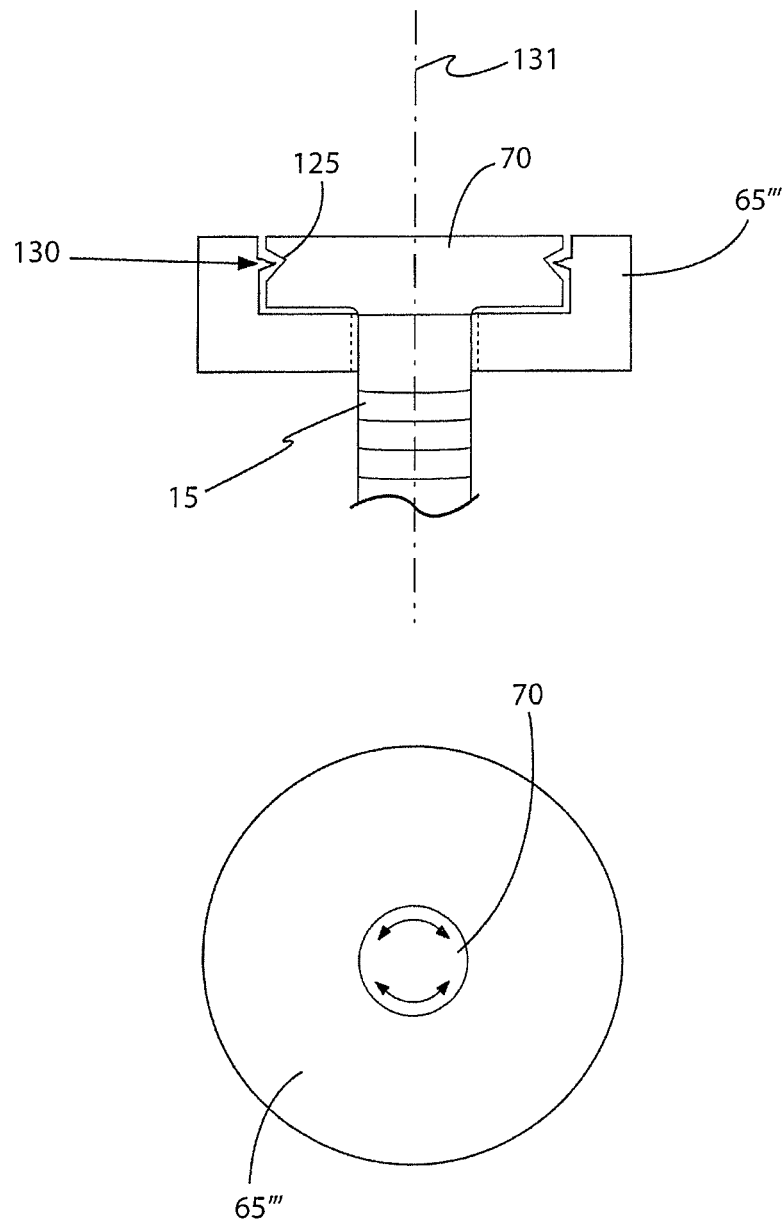

FIG. 14 depicts an additional arrangement of the head element 70 and tissue lock devices 65'''. As with previously described arrangements, the head element 70 is arranged at an end of the elongate element 15 of the tissue fastening device 10 opposite the delivery end 25. In the embodiments shown in FIG. 14, the head element 70 comprises at least one depression 125 and the tissue lock device 65''' comprises at least one protrusion 130 that corresponds to and is structured and arranged to engage the depression 125. In this manner, when the head element 70 is fully inserted into the tissue lock devices 65''', the depression 125 engages the protrusion 130 so that axial movement of the tissue fastening device 10 relative to the tissue lock device 65''' is inhibited. However, although axial movement is inhibited, the engagement of the depression 125 and the protrusion 130 permits the tissue fastening device 10 to swivel within the tissue lock device 65'''. In embodiments, at least a portion of at least one of the tissue fastening device 10 and the tissue lock device 65''' is composed of resilient material, such that a snap-fit is achieved with the depression 125 and the protrusion 130 when the tissue fastening device 10 is inserted into the tissue lock device 65'''.

In embodiments, when the tissue lock device 65''' clips (e.g., snaps) onto the head element 70 via the depression 125 and the protrusion 130, there is a small amount of play between the depression 125 and the protrusion 130 so that the tissue lock device 65''' can swivel about a longitudinal axis 131, e.g., of the head element 60 and/or elongate element 15. The amount of play can be designed to permit a slight amount of angular deflection (e.g., up to about five degrees) of the tissue lock device 65''' relative to the longitudinal axis 131 to alleviate torque forces on the tissue adjacent the tissue lock device 65''' to limit tissue necrosis. In additional embodiments, a tool or other mechanism may be provided to disengage the connected the depression 125 and the protrusion 130.

Exemplary Methods of Use

The following describes an example of a possible method of using the Knotless Locking tissue fastening device, but does not limit other potential applications of the device. Two ends or segments of tendon, ligament, bone, or other tissue are freshened with a sharp instrument to optimize apposition. The areas of apposition can be brought into and held in apposition with a variety of instruments including but not limited to bone clamps, hemostats, tacking sutures, or pins. The needle 45 on the delivery device 40 is delivered through the apposed tissue, pulling the diltator cone 50 atraumatically through the tissue via the connected suture 55 and creating a path for the tissue fastening device 10. The tissue fastening device 10 is locked at this point relative to the tissue by integrated tissue locking features 60 or a separate tissue lock device 65.

Once the tissue fastening device 10 is deployed in position within the tissue, the lock device 35 is placed at the junction of the dilator cone 50 and the tissue fastening device 10. The lock device 35 is then secured relative to the tissue fastening device 10. Once the tissues are approximated and the tissue fastening device 10 is locked in place, the delivery device 40 can be separated from the tissue fastening device 10 and discarded. Tissue alignment and positioning, device delivery, and locking may be performed with or without the aforementioned device. This is essentially similar to a single interrupted suture repair in function, and may be repeated to provide multiple points of attachment between the two ends or segments of tissue.

An alternate approach is to use a Linked tissue fastening device. In this case, once the Device is pulled through until the last tissue fastening device is in position and locked relative to the tissue with tissue locking features or a tissue lock device, a lock device can be deployed. This deployed and locked tissue fastening device could then be separated from the delivery device, which could then be used for the next suture in a rapid interrupted repair. Alternatively, the delivery device could be left connected to the deployed and locked Tissue fastening Device and used to deploy the next tissue fastening device in a running fashion repair.

Figure 15:
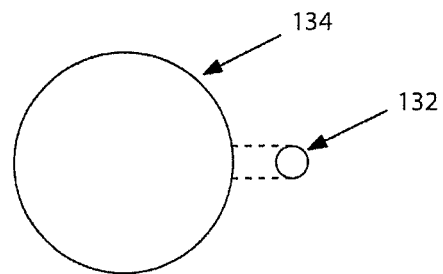
Figures 16, 17:
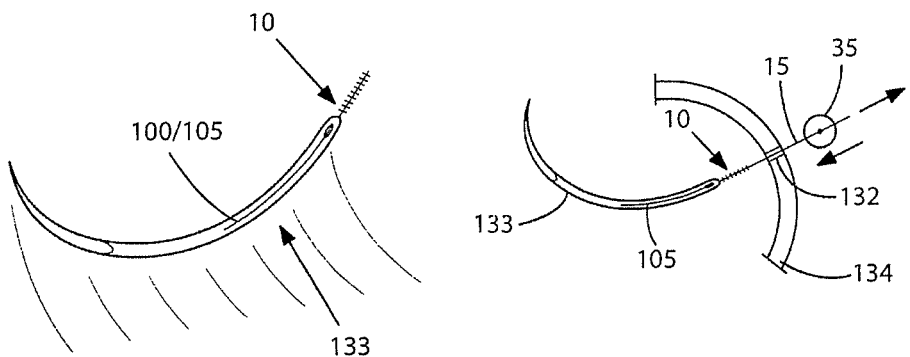
Figures 18, 19:
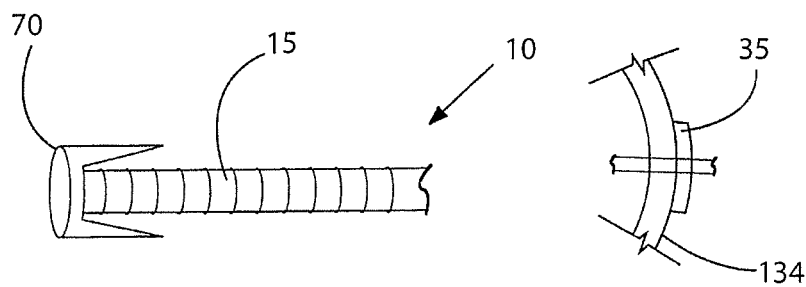

FIGS. 15-18 show a method for implanting an eyelid support system in accordance with aspects of the invention. As depicted in FIG. 15, a hole 132 is drilled through the lateral orbital rim 134 (e.g., bone). As depicted in FIG. 16, a tissue fastening device 10 is arranged to engage a portion of the canthus 133 (e.g., tissue near the eye), such as, for example, the lateral canthus. For example, the end 100 having barbs 105 may be inserted into the tissue of the canthus 133. At the step depicted in FIG. 17, the delivery end 25 of the tissue fastening device 10 is inserted into and through the hole 132 in the orbital rim 134. On the side of the orbital rim 134 opposite the canthus 133, the delivery end 25 of the tissue fastening device 10 is inserted through a locking device 35. As depicted in FIG. 18, the locking device 35 may be placed flush against the bone, and the elongate element of the tissue fastening device 10 may be pulled through the locking device 35, drawing the canthus 133 toward the orbital rim 134 until a desired spatial relationship between the canthus 133 and the orbital rim 134 is achieved. The tissue fastening device 10 and the locking device 35 may be locked relative to one another using any suitable locking mechanism, including those described herein (e.g., ratchet (e.g., zip) type locking, crimping, use of a sleeve, threaded, adhesive, melting, etc.). In this manner, the canthus is moved to a desired position relative to the bone, and fixed in that position.

FIG. 19 shows an embodiment of a head element 70 that can be used with the tissue fastening device 10 used in the method according to FIGS. 15-18. The head element 70 may include protrusions that serve to anchor the tissue fastening device 10 in the canthus, such as barbs 105 as described with respect to FIGS. 10-12.

According to another aspect of the invention, there is a method for facial rejuvenation that uses, for example, the tissue fastening device 10 and locking device 35 depicted in FIGS. 10-13. In this method, the delivery tube 110 is used to insert the tissue fastening device 10 into facial tissue. When the tissue fastening device 10 is properly located, the delivery tube 110 is removed, leaving the tissue fastening device 10 in the tissue and exposing the barbs 105. At this point, the barbs 105 are engaged to the facial tissue.

Still referring to FIGS. 10-13, the locking device 35 is connected to tissue such as the fascia of the skull or bone. The connection is made, for example, by suturing the platform 120 or the female member 115 to the tissue. The method includes passing the delivery end of the tissue fastening device 10 through the female member 115. The first tissue (e.g., face tissue engaged by the barbs 105) is drawn toward the second tissue (e.g., skull fascia sutured to the locking member 35) by moving the elongate element 15 of the tissue fastening device 10 through the locking device 35. When the appropriate spatial relationship between the first and second tissue is achieved, the tissue fastening device 10 is axially locked relative to the locking device 35 in one of the manner described herein.

FIGS. 20-23 demonstrate another method according to aspects of the invention, in which the tissue fastening device 10 is used to close a wound (e.g., an opening 160 in the abdominal fascia). At FIG. 20, the needle 45 is passed through tissue on a first side 165 of the opening 160, passed across the opening, and passed through tissue on a second side 170 of the opening 160 opposite the first side 165. This draws the elongate body 15 of the tissue fastening device 10 through the first tissue, across the opening 160, and through the second tissue. The head end of the tissue fastening device 10 is prevented from pulling through the first tissue by way of the tissue lock device 65 that is integral with the tissue fastening device 10 or, alternatively, which is arranged on the tissue fastening device prior to the needle being drawn through the portions of tissue, e.g., as described with respect to FIGS. 2-7.

Figure 20:
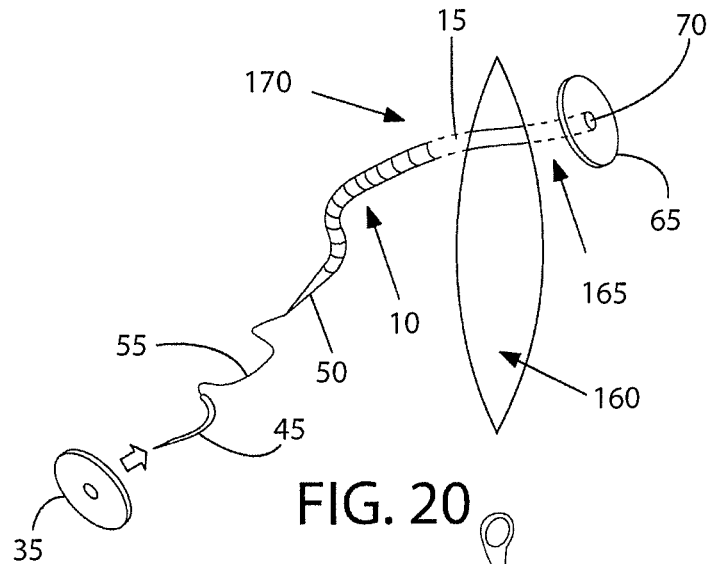
Figures 21, 22:
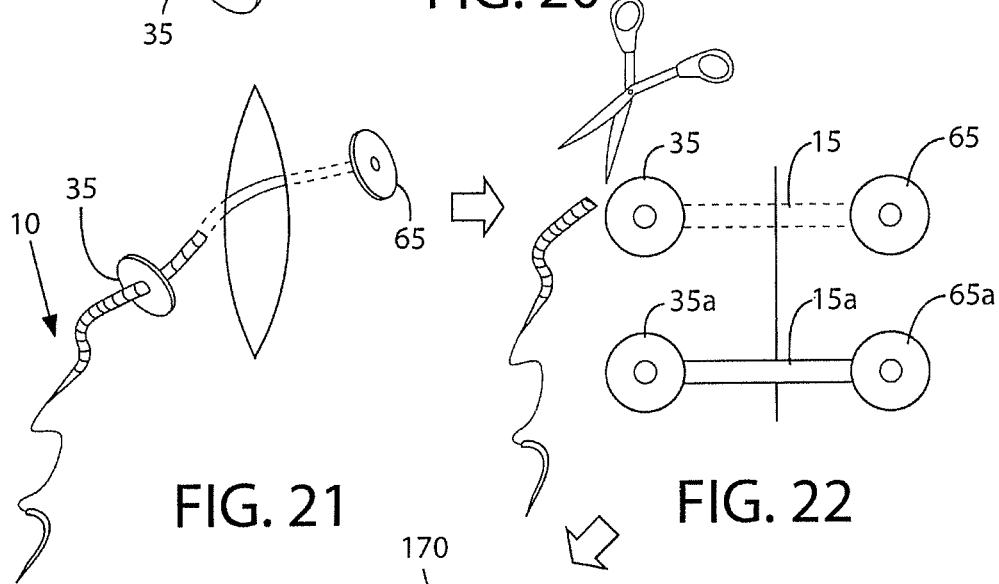

As depicted in FIGS. 20 and 21, the needle 45 is directed through a locking device 35, and the locking device 35 is slid up the elongate element 15 of the tissue fastening device 10, e.g., the lock device 35 is moved axially along the elongate element 15 toward the head element 70. The first and second sides 165, 170 of the opening 160 are drawn closer together as the locking device 35 moves further up the tissue fastening device 10 (e.g., toward the head element 70) due to the lock device 35 and the tissue lock device 65 exerting pressure toward one another on the tissue on the opposite sides 165, 170 of the opening 160. As depicted in FIG. 22, when the desired spatial relationship between the first and second sides 165, 170 of the opening 160 is achieved, the locking device 35 is axially locked relative to the tissue fastening device 10, and the remaining free end of the elongate element 15 of the tissue fastening device is cut flush to the locking device 35 and discarded. In this manner, the system according to aspects of the invention may be used to create an interrupted suture. The process may be repeated any number of times using a new tissue fastening device 10 (e.g., shown as 15*a*, 35*a*, and 65*a* in FIG. 22) each time, resulting in a plurality of interrupted sutures.

Figure 23:
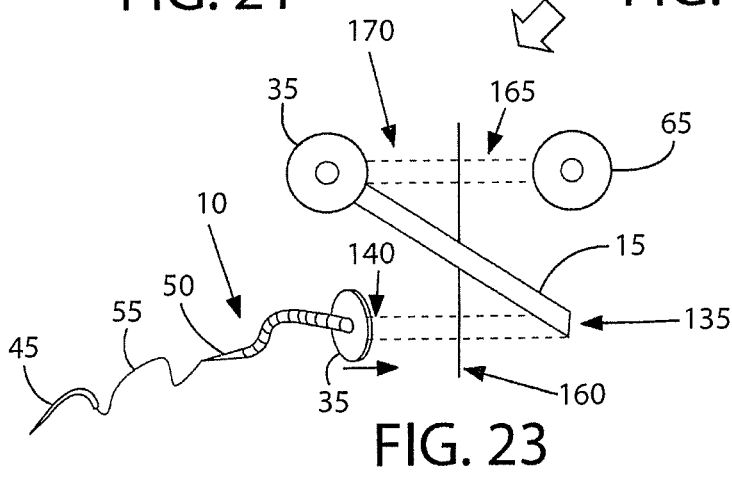

Alternatively to an interrupted suture, aspects of the invention can be used to make a running suture, as in FIG. 23. For example, instead of cutting the tissue fastening device as in FIG. 22, a second stitch may be made with the same tissue fastening device 10. More specifically, as depicted in FIG. 23, the needle may be passed through the tissue on the first side 165 of the opening 160 at a second location 135, extended across the opening, and passed through the tissue on the second side 170 of the opening 160 at a second location 140. Then, the needle 45 may be passed through a second locking device 35, and the second locking device 35 may be slid along the elongate element to draw the first location 135 and second location 140 together. This process may be repeated as many times as desired. In this manner, a single tissue fastening device 10 may be used with plural locking devices 35 to create a running suture. Moreover, because each locking device is ultimately axially fixed relative to the tissue fastening device 10, the running suture has the security of an interrupted suture.

Figure 24:
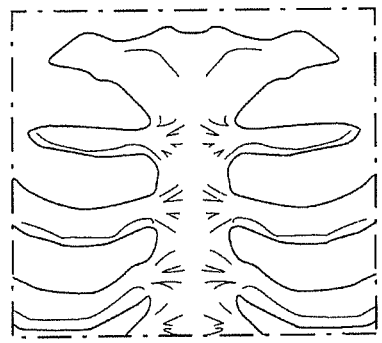
Figure 24:
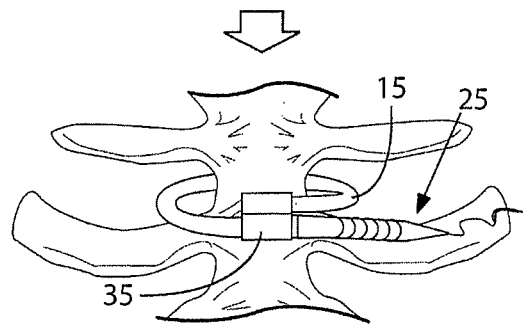

FIG. 24 shows another method according to aspects of the invention. In embodiments, a tissue fastening device 10 similar to that show in FIGS. 4-6 and 8 may be used to close a split sternum. In this method, the first side 150 and second side 155 of a split sternum are approximated. The elongate element of the tissue fastening device 10 is wrapped around the first side 150 and second side 155, and the delivery end of the tissue fastening device 10 is passed through the locking device 35. The elongate element 15 is drawn through the locking device 35, drawing the first side 150 and second side 155 of the sternum together. When the desired spatial relationship between the first side 150 and second side 155 is achieved, the tissue fastening device 10 is axially locked relative to the locking device 35 in one of the manners described herein. The end of the tissue fastening device 10 may be cut flush with the locking device 35 and discarded. In embodiments, the assembly device 80 (described with respect to FIG. 9) may be used to draw the elongate element 15 through the locking device 35 until a predetermined tensile force is achieved. The assembly device 80 may also be used to cut the tissue fastening device 10 may be cut flush with the locking device 35.

Figure 25A:
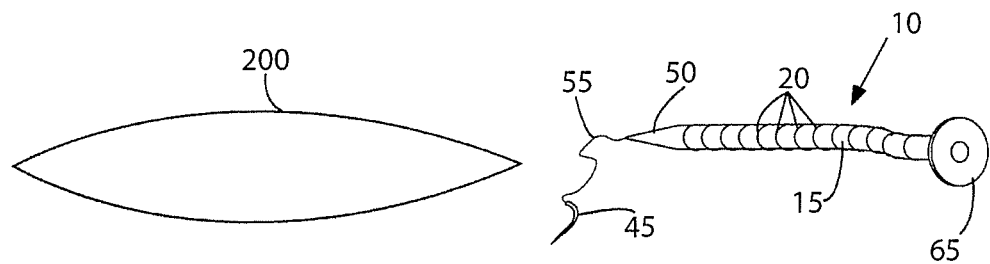
Figure 25B:
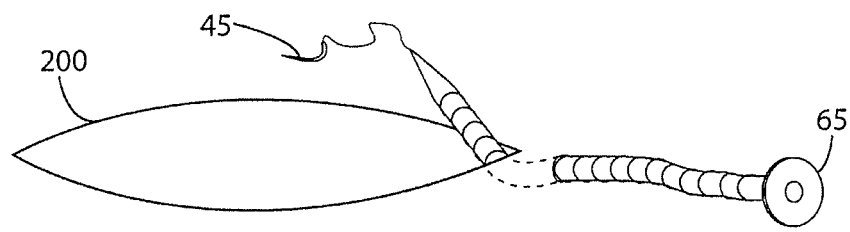
Figure 25C:
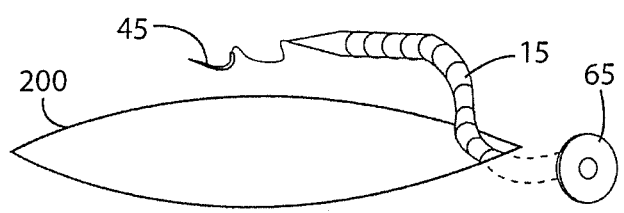
Figure 25D:
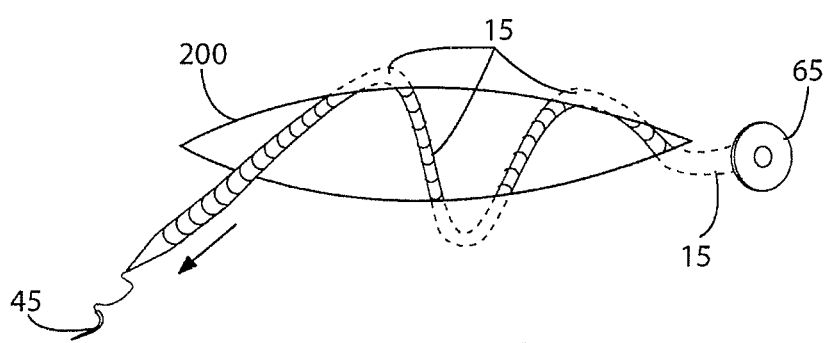
Figure 25E:
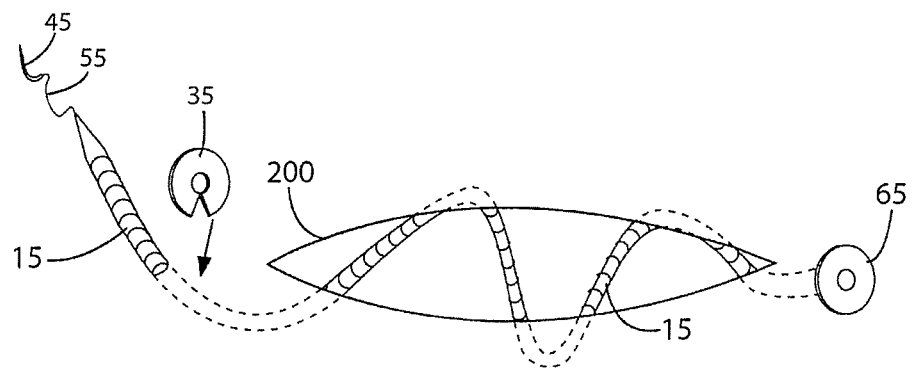
Figure 25F:
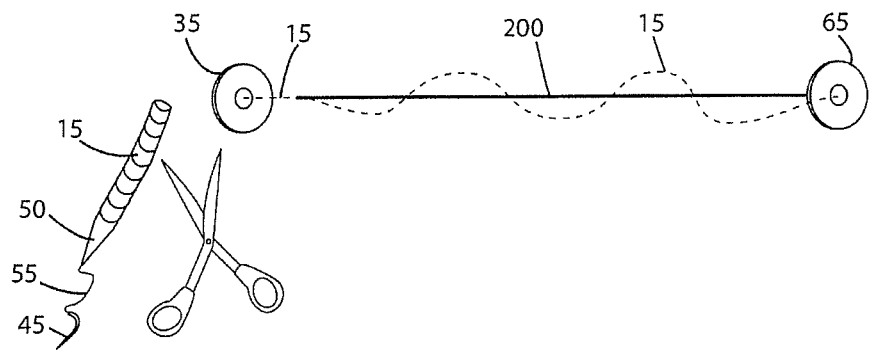
Figure 25G:
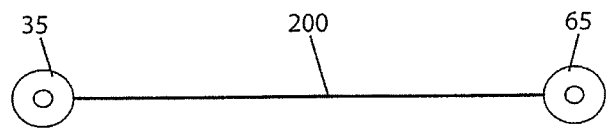

FIGS. 25A-G depict an exemplary process of using a zip suture for intracuticular skin closure in accordance with aspects of the invention. In implementations, the elements of the tissue fastening device 10 may be scaled to a sufficiently small size for superficial placement, e.g., for closing an opening 200 in the skin. As shown in FIG. 25A, the needle 45 is used to enter the wound opening 200 from the outside about 1 cm to about 2 cm away. As depicted in FIGS. 25B and 25C, the elongate element 15 is pulled through until the tissue lock device 65 meets the skin. As shown in FIG. 25D, the needle 45 is used to weave the elongate element 15 back and forth through the dermal tissue while providing some axial tension on the elongate element 15. As depicted in FIGS. 25E and 25F, the elongate element 15 is placed through the skin about 2 cm outside of the opening 200, the elongate element 15 is pulled to close the opening 200, and a lock device 35 is moved onto the elongate element 15 to a position flush against the skin, whereby the mating features 30 engage the locking features 20 to substantially lock the lock device 35 on the elongate element 15 and against the skin. The free end of the elongate element 15 is cut flush with the lock device 35. To remove the tissue locking system 10, the tissue lock device 65 and lock device 35 may be lifted from the skin and the elongate element 15 cut adjacent the tissue lock device 65 and lock device 35, and the remaining portion of the elongate member dissolves in the body.

FIGS. 26A and 26B depict a situation in which the elongate element 15 is arranged at a shallow angle relative to the outer surface 250 of the tissue. This shallow angle can cause the lock device 35 and/or tissue lock device 65 to also be angle relative to the outer surface 250 of the tissue, which can cause the lock device 35 and/or tissue lock device 65 to impart localized pressure at a portion 260 of the tissue, e.g., dig into the tissue.

Figure 27:
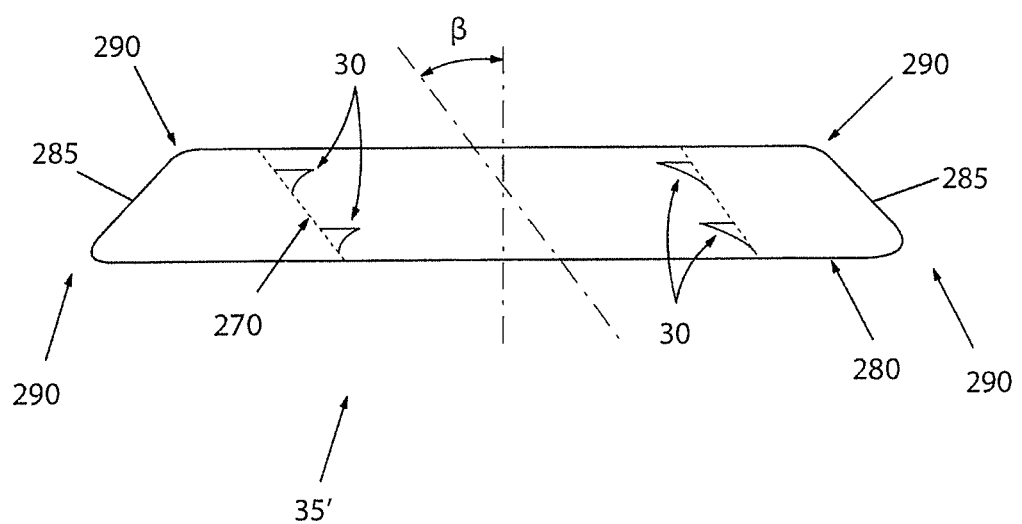

FIG. 27 shows a lock device 35' in accordance with aspects of the invention in which a through-hole 270 is angled at a non-perpendicular angle β relative to a bottom surface 275 of the lock device 35'. In embodiments, the angle β is in a range of about 30° to about 60°, although the invention is not limited to this range and any suitable angle may be used within the scope of the invention. As shown in FIGS. 28A and 28B, the angled hole 270 permits the bottom surface 280 of the lock device 35' to sit flush against the outer surface 250 of the tissue without imparting a localized pressure in the tissue. In further embodiments, the sidewalls 285 of the lock device 35' may be tapered to avoid snags and/or the corners 290 of the lock device 35' may be rounded to further avoid snags and/or digging into the tissue.

Figure 29A:
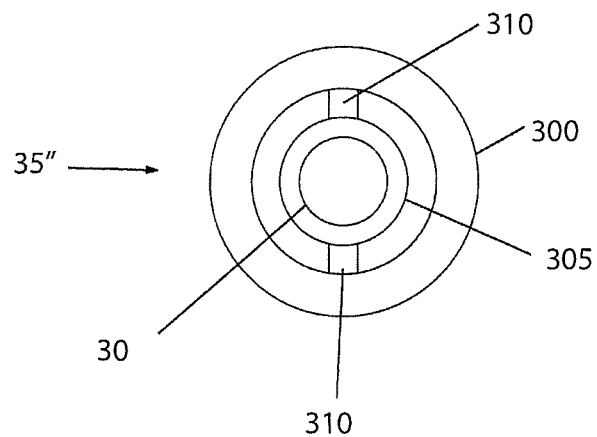
Figure 29B:
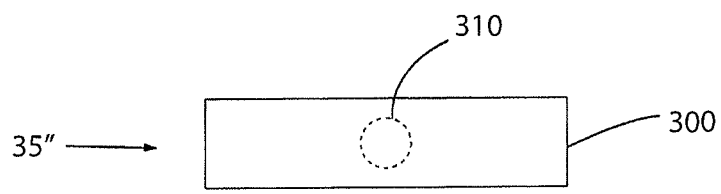
Figure 29C:
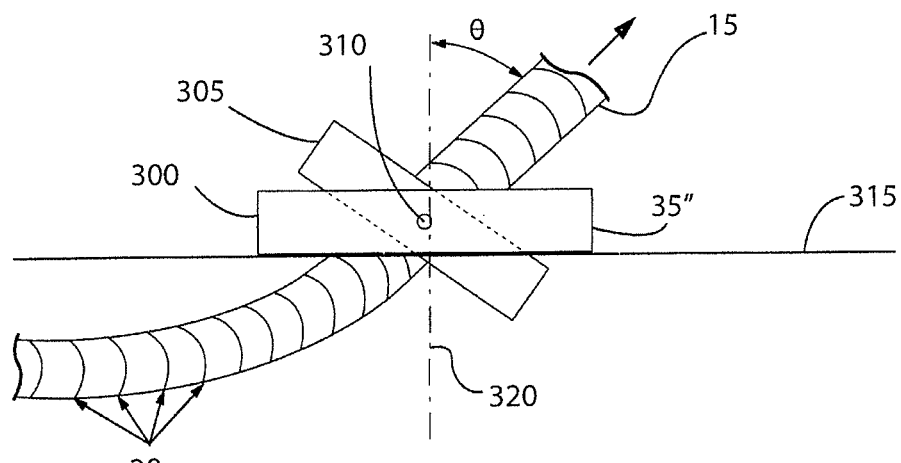

As shown in FIGS. 29A-C, and in accordance with further aspects of the invention, the lock device 35" may comprise a body 300 and a swivel head 305 that engages the elongate element 15. The swivel head 305 may be connected to the body 300 by a connection mechanism 310 that permits the swivel head 305 to rotate relative to the body 300. For example, the body 300 may comprise a relatively large external circular washer, and the swivel head 305 may comprise a relatively smaller internal circular washer. The body 300 is designed to sit flush against the tissue 315, while the swivel head 305 designed to engage the elongate element 15 while permitting the elongate element 15 to pass through the body 300 at an angle θ relative to a central axis 320 of the body 300, which allows the force vector and security vector of the tissue device 10 to be arranged at appropriate angles. The swivel head 305 may engage the elongate member in any manner described herein, e.g., via locking features 20 and mating features 30. The connection mechanism 310 may be similar to mechanism 66 described with respect to FIGS. 4D-4F, or may comprise any other desired structural arrangement for permitting rotational movement of the swivel head 305 relative to the body 300. The rotation of the swivel head 305 may be limited by appropriate structures, such as one or more limit stops.

Figure 30:
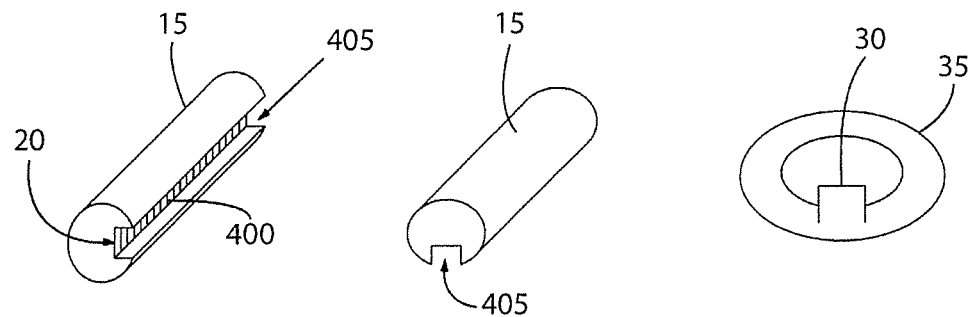

FIG. 30 shows an arrangement of locking features 20 and mating features 30 in accordance with aspects of the invention. In embodiments, the locking features 20 may comprise one or more teeth 400 (e.g., ridges, catches, etc.) that are located within a groove 405 in the elongate element 15. In this manner, the teeth 400 are at a concave portion rather than a convex portion of the outer surface of the elongate element 15, such that the teeth are less likely to snag and/or harm the adjacent tissue. FIG. 30 also shows a lock device 35 having a mating feature 30 comprising at least one inwardly extending protrusion 410 of an annular body 415, wherein the protrusion 410 is structured and arranged to engage the teeth 400 to permit one-way axial movement of the lock device 35 on the elongate element 15.

In embodiments, the locking features 20 and mating features 30 may be similar to those described in U.S. Patent Application Publication 2011/0022050 and/or International Patent Application Publication No. WO 2010/108050 the contents of both publications being incorporated by reference herein in their entirety. For example, the elongate element 15 (e.g., zip suture) may have locking features 20 such as ball shapes, cylindrical or circular shapes, pointed conical shapes, barbs, roughening, knurling, protrusions, indentations, grooves, ridges, teeth, or any other shape. In some instances, some of locking features (e.g., bumps, teeth or ridges) may be buried so that they do not protrude from the outermost surface of the elongate element 15. The elongate element 15 may be round or elliptical with hidden locking features which may prevent them from catching on tissue. For example, the elongate element 15 may include one or more large channels or indentation, in which one or more locking features 20 may be provided. In some instances, the elongate element 15 may include one or more linkages, like a chain.

In some embodiments, the elongate element 15 may be inlayed with fibers, fine wire, mesh, or other additives which may increase the strength of the elongate element 15, and thereby the tissue device 10. Additives may make the suture stiffer to longitudinal forces and/or provide any other desired material properties, such as stiffness, flexibility, strength, or elasticity to the suture. In some instances, the fibers or other additives may be like mesh used in other applications. It may allow strength without limiting or minimally impacting flexibility.

Figure 31:
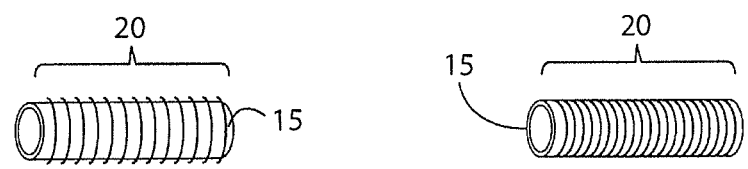

Alternatively to being located within the groove 405, the teeth 400 or other locking features 20 may be arranged on a convex outer surface of the elongate element 15, as shown in FIG. 31, and may extend around a portion or the entire perimeter of the elongate member.

Figure 32:
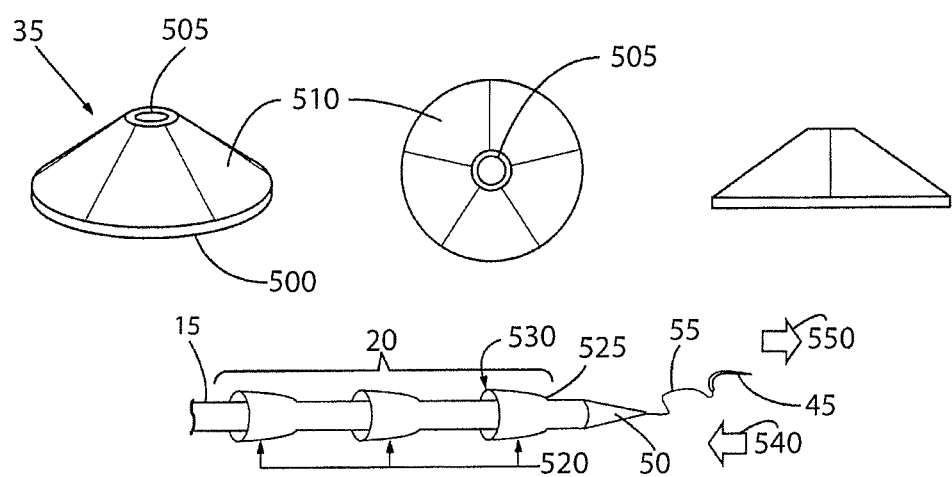

FIG. 32 shows cone-shaped lock device 35 comprising a rim 500, hole 505, and angled walls 510 between the rim 500 and hole 505. In this embodiment, the mating feature 30 comprises the edges of the walls 510 that define the perimeter of the hole 505. FIG. 32 also shows an elongate element 15 comprising locking features 20 that comprise tapered elements 520 having a narrow end 525 and a wide end 530. In operation, the lock device 35 is moved along the elongate element 15 in a direction 540 by first drawing the narrow end 525 and then the wide end 530 of a particular tapered element 520 through the hole 505. The hole 505 is larger than the narrow end 525 and smaller than the wide end 530, such that the wide ends 530 compresses to fit through the hole 505. After the wide end 530 of a particular tapered element 520 passes through the hole 505 in the first direction 540, the relative sizes of the wide end 530 and hole 505 prevent the particular tapered element 520 from passing back through the hole 505 in the opposite direction 550, thereby effectively locking the lock device 35 relative to the elongate element 15. The lock device 35 is designed for the rim 500 to sit against the tissue.

Figure 33A:
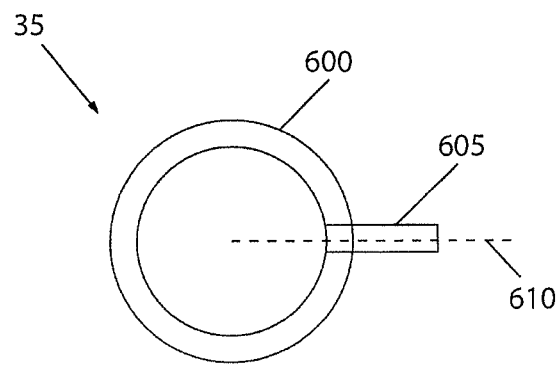
Figure 33B:
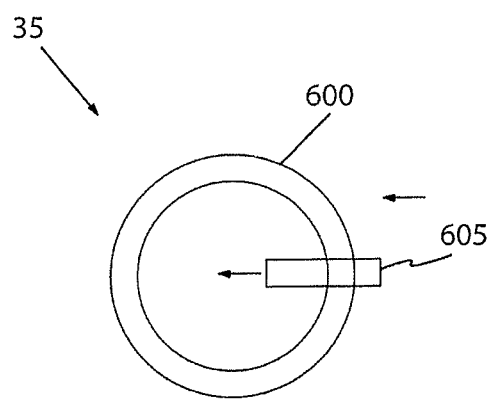

FIGS. 33A and 33B show a lock device 35 in accordance with further aspects of the invention. In embodiments, the lock device 35 comprises an annular body 600 and a plunger 605 that is axially moveable in a radial direction 610 of the annular body 600. In operation, the delivery end of the elongate element 15 is inserted into the annulus of the annular body 600 and the annular body 600 is moved along the elongate element 15 with the plunger 605 in a retracted position, as shown in FIG. 33A. When the annular body 600 is located at the desired position along the length of the elongate element 15, the plunger 605 is depressed, e.g., moved toward the center of the annular body 600, as shown in FIG. 33B. The plunger 605 may be structured and arranged to engage locking features 20, such as teeth, holes, or indentations, of the elongate element 15 to prevent back migration of the lock device 35 on the elongate element 15. For example, depressing the plunger 605 against the elongate element 15 may fix the lock device relative to the elongate element 15 such that the lock device cannot move in either direction along the elongate element, which prevents unwanted tightening of the tissue device 10 such as when the patient coughs or otherwise moves. Alternatively to depressing the plunger 605 inward, the lock device 35 may comprise a linkage mechanism that causes a mating feature 30 to engage a locking feature 20 of the elongate element 15 when the plunger 605 is pulled radially outward from the annular body 600.

FIG. 34A shows the lock device 35 may comprise an annular body 700 having a through hole 705 for receiving and engaging the elongate element 15. A bottom surface 710 of the lock device 35 is provided with an undulating profile having visible concave and convex features that are arranged to lie against the tissue when the lock device 35 is engaged with the elongate element 15. The concave portions reduce pressure on portions of the adjacent to promote blood flow in the tissue to inhibit or prevent tissue necrosis. In embodiments, the concave and/or convex portions of the surface 710 are rounded to avoid sharp points that might cause discomfort when pressed against the tissue.

FIG. 34B shows a lock device 35 similar to that of FIG. 34A but having an undulating top surface 715 in addition to an undulating bottom surface 710. In this manner, the surgeon or technician applying the lock device 35 to the elongate element 15 need not worry about the orientation of the lock device 35, as both undulating surfaces 710 and 715 may be placed against the tissue. The lock device 35 shown in FIGS. 34A and 34B may include any of the other features of the various lock devices 35 described herein including, but limited to, mating feature(s) 30, angled hole 270, tapered sidewalls 285, rounded corners 290, swivel head 305, and plunger 605. Conversely, one or both undulating surfaces 710, 715 may be used with any of the other lock devices 35 described herein.

As depicted in FIG. 35A, the lock device 35 may comprise an annular body 800 having a through hole 805 for receiving and engaging the elongate element 15. A bottom surface 810 of the lock device 35 is provided with a saw-tooth profile having pointed features that are arranged to lie against the tissue when the lock device 35 is engaged with the elongate element 15. The saw-tooth profile having pointed features provides a stronger grip of the lock device to the tissue compared to the rounded features shown in FIGS. 34A-B and also compared to a substantially flat surface 280 shown in FIG. 27, such that a lock device 35 having a saw-tooth profile bottom surface 810 may be used when a strong and secure grip on the tissue is desired, e.g., in tendon and ligament repair.

FIG. 35B shows that the lock device 35 may have the saw-tooth profile on both the both surface 810 and top surface 815 of the annular member 800 with hole 805. FIG. 35C shows that the lock device 35 may comprise the annular body 800 having a through hole 805 and further comprising two barbs 820 at the bottom surface rather than a saw-tooth profile. Any number of protrusions having any desired shape may be provided on the bottom and/or top surface of the lock device to promote a stringer grip on the adjacent tissue. The lock device 35 shown in FIGS. 35A-C may include any of the other features of the various lock devices 35 described herein including, but limited to, mating feature(s) 30, angled hole 270, tapered sidewalls 285, rounded corners 290, swivel head 305, and plunger 605. Conversely, one or both undulating surfaces 710, 715 may be used with any of the other lock devices 35 described herein.

As depicted in FIG. 36, the lock device 35 may comprise an annular body 900 having a through hole 905 for receiving and engaging the elongate element 15. A bottom surface 910 of the lock device 35 is provided with at least one of: roughening 915 and one or more small holes 920. The roughening 915 may be similar to that used in an artificial hip to allow the adjacent tissue to grip the lock device 35 and allow fibrous attachments to form on the lock device 35 body 900, thereby increasing the security of the lock device 35 against the tissue. The small hole(s) 920 may extend only partially into the body 900 or completely through the body 900, and allow tissue to grow into the body 900, thereby increasing the security of the lock device 35 against the tissue. The lock device 35 shown in FIG. 36 may include any of the other features of the various lock devices 35 described herein including, but limited to, mating feature(s) 30, angled hole 270, tapered sidewalls 285, rounded corners 290, swivel head 305, and plunger 605. Conversely, at least one of: roughening 915 and one or more small holes 920 may be used with any of the other lock devices 35 described herein.

Figure 37A:
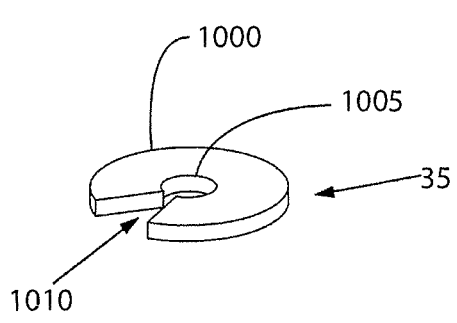
Figure 37C:
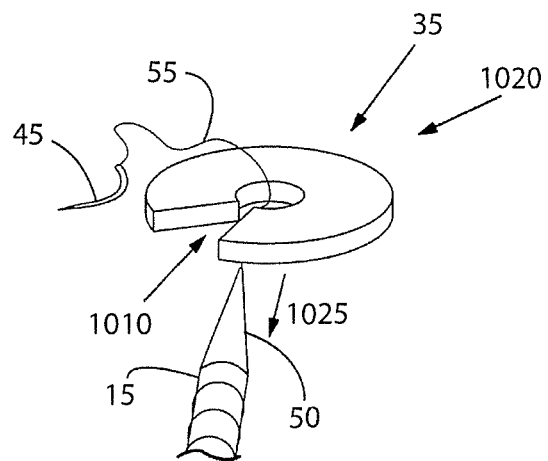
Figure 37B:
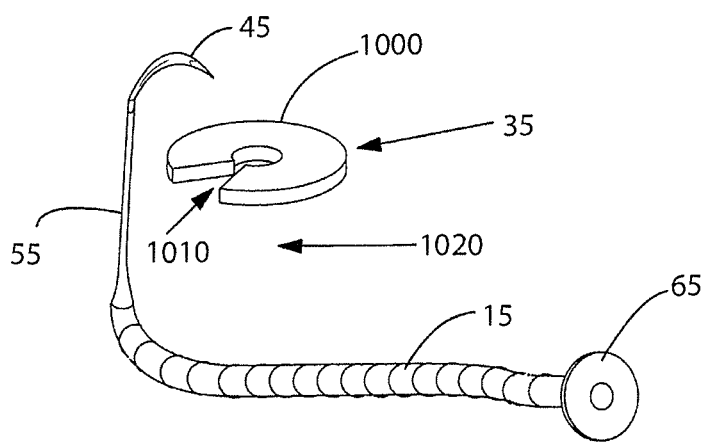

FIGS. 37A-C show a lock device 35 in accordance with further aspects of the invention. In embodiments, the lock device 35 comprises an annular body 1000 having a through hole 1005 for receiving and engaging the elongate element 15. The lock device 35 also comprises a radial slit 1010 that is sized slightly larger than the delivery suture 55 but small than the elongate element 15. In this manner, the lock device 35 may be moved onto the elongate element 15 by first passing the delivery suture 55 through the slit 1010 and into the hole 1005 with a sideways motion 1020 (as shown in FIG. 37B) and then moving the lock device 35 down onto the elongate element 15 with an axial motion 1025 (as shown in FIG. 37C). In this manner, the surgeon applying the lock device need not feed the needle 45 through a hole 1005 (e.g., thread a needle), but instead can hold the needle 45 and/or delivery suture 55 and move the lock device 35 sideways onto the suture 55 at any desired location via the slit 1010. For example, one person may hold the needle 45 and/or delivery suture 55 while another person moves the lock device 35 onto the suture 55. This permits a faster application of the locking device 35 to the elongate element 15. This also protects the needle 45 from damage that may result from attempting to thread the needle 45 through the hole 1005. The slit 1010 may have any desired shape, such as parallel sidewalls or a wedge shape with sidewalls arranged at an acute angle to one another.

Figure 38:
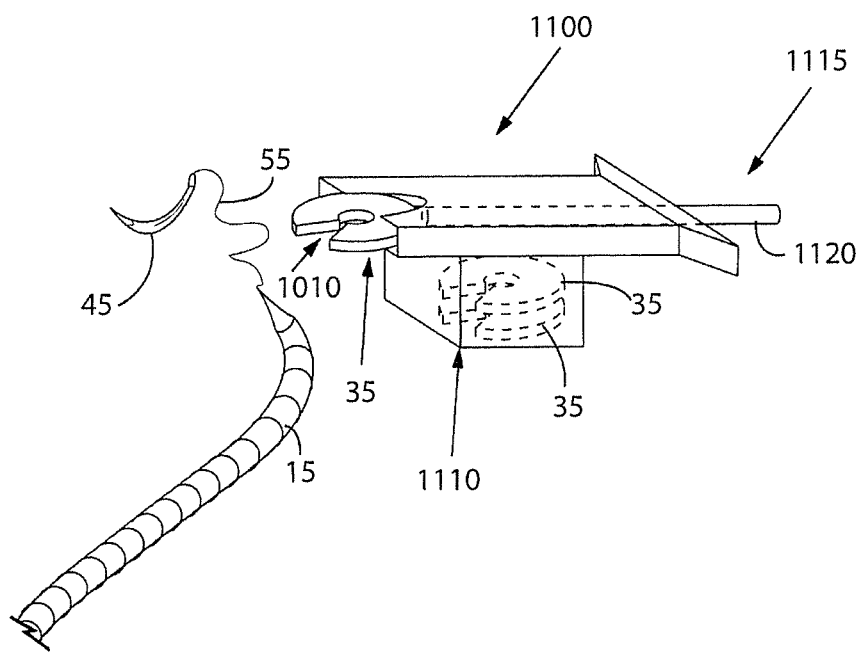

FIG. 38 shows a lock device gun 1100 in accordance with aspects of the invention. In embodiments, the lock device gun 1100 is structured and arranged to hold a plurality of lock devices 35 each having a slit 1010. The lock device gun 1100 may comprise, for example, a magazine 1110 for holding a plurality of lock devices 35 each having a slit 1010. In embodiments, the lock device gun 1100 also comprises an actuator 1115 for moving one of the lock devices 35 out of the gun 1100 and toward the delivery suture 55 of the tissue device 10. The actuator 1115 may comprise, for example, a plunger 1120 that takes a lock device 35 from a the magazine 1110 and pushes the lock device 35 out of an opening of the gun 1110 with the slit 1010 facing outward. The actuator 1115 and/or magazine 1110 may incorporate springs for automatic re-loading of a next lock device 35 after a previous lock device 35 is pushed out of the gun 1100. The gun 1100 may comprise guide element, such as rails, tabs, rollers, etc., the cause the lock device 35 being pushed out by the actuator 1115 to have its slit 1010 facing outward, e.g., in an axial direction 1150 away from the gun 1100, in order to align the slit 1010 with the delivery suture 55 of the tissue device 10. In this manner, the gun 1100 may be used to quickly and easily apply a plurality of lock devices 35 to tissue device, such as in a running or uninterrupted suture (e.g., as shown in FIG. 2B, FIG. 23, etc.).

The invention is not limited to the exemplary methods described herein. Instead, different processes may be practiced within the scope of the invention. For example, additional steps may be added, steps may be performed in a different order, etc. The systems and methods described herein according to aspects of the invention may be used in the following applications, although the invention is not limited to only these applications: closure of the sternum following cardiac surgery; closure of thoracic incisions following thoracic surgery; tendon repair; ligament repair; closure of abdominal fascia; intradermal closure of skin or subcutaneous tissue and fascia; facial rejuvenation; eyelid suspension; and, repair of bone fractures.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A system for fastening tissue, comprising:
   a tissue fastening device comprising an elongate element;
   a delivery device comprising a cone, suture, and needle arranged at a delivery end of the elongate element, wherein the suture is connected between the cone and the needle, and the suture is a different element than the elongate element;
   a tissue lock device arranged at an end of the elongate element opposite the delivery end;
   a locking feature near the delivery end; and
   a lock device having a mating feature that corresponds to the locking feature;
   wherein when the delivery device is passed through the lock device, the mating feature engages the locking feature and locks the lock device in an axial direction along the elongate element,
   the tissue lock device comprises a groove,
   the elongate element comprises a head element that fits within the groove such that a top surface of the head element is substantially flush with a top surface of the tissue lock device, and
   the head element extends outward relative to the elongate element in a radial direction and has a larger dimension than the elongate element in the radial direction.

2. The system of claim 1, wherein
   the tissue lock device comprises a protrusion in the groove,
   the head element comprises a depression that corresponds to the protrusion, and
   the protrusion engages the depression to prohibit axial movement of the head element out of the groove when the head element is arranged in the groove.

3. The system of claim 2, wherein the head element may spin within the groove when the protrusion engages the depression.

4. The system of claim 1, wherein the delivery device is passed through the lock device by one of:
   threading the needle through a hole in the lock device; and
   passing the suture through a radial slit and into a though-hole in the lock device.

5. The system of claim 1, wherein the elongate element is structured and arranged as a running suture, the tissue lock device is arranged at a beginning of the running suture, and a plurality of the lock devices are arranged on an engage the elongate element at a plurality of locations along the running suture.

6. The system of claim 1, wherein the lock device comprises an angled hole that is structured and arranged to receive and engage the elongate element at an acute angle relative to a central axis of the lock device.

7. The system of claim 1, wherein the lock device comprises an annular body comprising tapered sidewalls and rounded corners.

8. The system of claim 1, wherein the lock device comprises an annular body and a swivel head rotatably attached within the annular body, wherein the swivel head is structured and arranged to receive and engage the elongate element at an acute angle relative to a central axis of the annular body.

9. The system of claim 1, wherein:
   the locking feature comprises at least one tapered element having a narrow end and wide end on the elongate element,
   the lock device comprises a cone comprising a rim structured and arranged to sit against tissue, angled sidewalls, and a hole, and
   the hole is larger than the narrow end of the tapered element and smaller than the wide end of the tapered element.

10. The system of claim 1, wherein the elongate element comprises a groove and the locking features are arranged within the groove such that the locking features are not on an outermost surface of the elongate element.

11. The system of claim 10, wherein:
the elongate element has an oval or round cross sectional profile including the groove; and
the lock device comprises a member having an annulus comprising the mating feature, the annulus and mating feature corresponding in shape to oval or round cross sectional profile including the groove.

12. The system of claim 1, wherein the lock device comprises a plunger that is structured to engage the elongate element when depressed inward or pulled outward, the plunger preventing the lock device from moving along the elongate element when engaged.

13. The system of claim 1, wherein the lock device comprises one of:
an undulating bottom surface having rounded concave and convex portions that are structure and arranged to lie against the tissue to reduce pressure on portions of the tissue within the concave portions;
a saw-tooth profile bottom surface that is structured and arranged to lie against and dig into the tissue to secure the lock device to the tissue; and
surface roughening and/or small holes that promote the in-growth of tissue into the lock device.

14. The system of claim 1, wherein the lock device comprises an annular member having a through hole and a radial slit, the radial slit being larger than the suture and smaller than the elongate member, such that the suture may be passed through the slit and into the hole.

15. The system of claim 14, further comprising a gun comprising a magazine for holding a plurality of the lock devices each having the axial slit, and an actuator for pushing one of the lock device outward from the gun with the axial slit facing outward.

16. The system of claim 1, wherein the tissue lock device is integral with the tissue fastening device comprising the elongate element.

17. The system of claim 1, further comprising an assembly device that is configured to engage the tissue fastening device and the lock device, pull the elongate element through the lock device to a predetermined force, and then cut the elongate element to be flush with the lock device.

* * * * *